United States Patent
Smith et al.

(10) Patent No.: US 7,612,068 B2
(45) Date of Patent: Nov. 3, 2009

(54) AROMATIC OXYPHENYL AND AROMATIC SULFANYLPHENYL DERIVATIVES

(75) Inventors: Garrick P. Smith, Valby (DK); Gitte K. Mikkelsen, Ballerup (DK); Kim Andersen, Ridgewood, NJ (US); Daniel R. Greve, Stenlose (DK); Jorgen Eskildsen, Copenhagen (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 455 days.

(21) Appl. No.: 10/551,737

(22) PCT Filed: Apr. 27, 2004

(86) PCT No.: PCT/DK2004/000290

§ 371 (c)(1),
(2), (4) Date: Jun. 5, 2006

(87) PCT Pub. No.: WO2004/096761

PCT Pub. Date: Nov. 11, 2004

(65) Prior Publication Data

US 2006/0235003 A1    Oct. 19, 2006

Related U.S. Application Data

(60) Provisional application No. 60/466,755, filed on Apr. 30, 2003.

(30) Foreign Application Priority Data

Apr. 30, 2003    (DK) ............................... 2003 00649

(51) Int. Cl.
| | | |
|---|---|---|
| A61K 31/5377 | (2006.01) | |
| A61K 31/506 | (2006.01) | |
| A61K 31/454 | (2006.01) | |
| A61K 31/4025 | (2006.01) | |
| A61K 31/40 | (2006.01) | |
| A61K 31/192 | (2006.01) | |
| C07D 413/02 | (2006.01) | |
| C07D 239/24 | (2006.01) | |
| C07D 401/02 | (2006.01) | |
| C07D 409/02 | (2006.01) | |
| C07D 207/08 | (2006.01) | |
| C07C 53/134 | (2006.01) | |

(52) U.S. Cl. ..................... 514/235.5; 514/247; 514/326; 514/422; 514/423; 514/567; 544/141; 544/335; 546/208; 548/527; 548/532; 562/400

(58) Field of Classification Search ............ 514/217.11, 514/317, 408, 484, 256, 446, 235.5, 247, 514/326, 422, 423, 567; 540/607; 544/333, 544/141, 335; 546/227, 208; 548/530, 527, 548/532; 549/76; 562/400

See application file for complete search history.

(56) References Cited

FOREIGN PATENT DOCUMENTS

| | | |
|---|---|---|
| EP | 1284257 A2 | 2/2003 |
| WO | WO-97/20553 A1 | 6/1997 |
| WO | WO-97/45115 A1 | 12/1997 |
| WO | WO-02/00602 A | 1/2002 |
| WO | WO-03/000646 A1 | 1/2003 |

OTHER PUBLICATIONS

Fred Wudl, Detection of Alkali Metal Ions via Optical Rotatory Dispersion; a Sensitive Test for Sodium in the Presence of Lithium and Potassium, J.C.S. Chem. Comm., 1972, 1229-1230.*
Bartl et al., "2-chloro-7-fluoro- and 2-chloro-3,7-difluoro-11-[4-(4-fluoroaralkyl)piperazino]-10,11-dihydrodibenzo-[b,f]thiepins and related compounds; long acting tranquillizers," Collection Czechoslovak Chem. Commun. 1981, 46, 141.
Fieser et al., "Synthesis of 6-methylaceanthrene," J. Am. Chem. Soc. 1952, 74, 536.
Gilman et al., "The yields of some organomagnesium and organolithium compounds," Recl. Trav. Chim. Pays-Bas 1935, 584.
Harder et al., "The molecular structure of 1-lithio-2-methoxybenzene in the solid state and in solution," J. Organomet. Chem. 1989, 364, 1-16.
Heresco-Levy et al., "Pilot-controlled trial of D-cycloserine for the treatment of post-traumatic stress disorder," The International Journal of Neuropsychopharmacology 2002, 5:301-307.
Iwao, "Directed lithiation of chlorobenzenes. Regioselectivity and application to a short synthesis of benzocyclobutenes," J. Org. Chem. 1990, 55, 3622-3627.
Javitt et al., "Amelioration of negative symptoms in schizophrenia by glycine," Am. J. Psychiatry 1994, 151, 1234-1236.
Leiderman et al., "Preliminary investigation of high-dose oral glycine on serum levels and negative symptoms in schizophrenia: an open-label trial," Biol. Psychiatry 1996, 39, 213-215.
Mitsunobu, "The use of diethyl azodicarboxylate and triphenylphosphine in synthesis and transformation of natural products," Synthesis 1981,1.

(Continued)

*Primary Examiner*—Kamal A Saeed
*Assistant Examiner*—Kristin Bianchi
(74) *Attorney, Agent, or Firm*—Stephen G. Kalinchak; Margaret M. Buck

(57) ABSTRACT

The present invention relates to compounds of formula I wherein the substituents are as defined below. The compounds of formula I are useful for the treatment of diseases such as schizophrenia, including both the positive and the negative symptoms of schizophrenia and other psychoses.

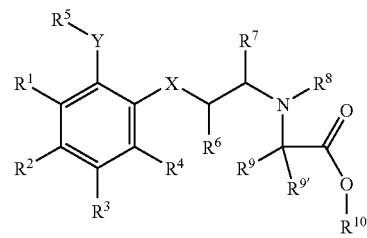

23 Claims, No Drawings

OTHER PUBLICATIONS

Rison et al., "Long-term potentiation and N-methyl-D-aspartate receptors: foundations of memory and neurologic disease?" Neurosci. Biobehav. Rev. 1995, 19, 533-552.

Samoshin et al., "Novel reaction: brominative aromatization of 2-alkyl(aryl)thio cyclohexanones," Tet. Lett. 1994, 35, 7413-7414.

Schopfer, "A general palladium-catalysed synthesis of aromatic and heteroaromatic thioethers," Tetrahedron 2001, 57, 3069-3073.

Stille et al., "Palladium-catalysed coupling of aryl halides with (trimethylstannyl)diphenylphosphine and (trimethylsilyl)diphenylphosphine," J. Org. Chem. 1987, 52, 748-753.

Truong et al., "Glycine involvement in DDT-induced myoclonus," Movement Disorders 1988, 3, 77-87.

Yaksh, "Behavioral and autonomic correlates of the tactile evoked allodynia produced by spinal glycine inhibition: effects of modulatory receptor systems and excitatory amino acid antagonists," Pain 1989, 37, 111-123.

Yeager et al., "An umpoled synthon approach to the synthesis of 2-aryloxyphenols," Synthesis 1995, 28-30.

* cited by examiner

AROMATIC OXYPHENYL AND AROMATIC SULFANYLPHENYL DERIVATIVES

CROSS-REFERENCE TO RELATED APPLICATIONS

This application is the 371 national stage of PCT/DK2004/000290, filed Apr. 27, 2004, and claims the benefit of priority under 35 U.S.C. § 119 of U.S. provisional application 60/466,755, filed Apr. 30, 2003, and Danish application PA 2003 00649, filed Apr. 30, 2003.

The present invention relates to novel compounds which are glycine transporter inhibitors and as such effective in the treatment of disorders in the CNS, such as schizophrenia.

BACKGROUND OF THE INVENTION

Glutamic acid is the major excitatory amino acid in the mammalian central nervous system (CNS), and acts through two classes of receptors, the ionotropic and metabotrobic receptors, respectively. The ionotropic glutamate receptors are divided into three subtypes based on the affinities of agonists for these receptors, namely N-methyl-D-aspartate (NMDA), (R,S)-2-amino-3-(3-hydroxy-5-methylisoxazol-4-yl)propanoic acid (AMPA) and kainic acid (or kainate) receptors.

The NMDA receptor contains binding sites for modulatory compounds such as glycine and polyamines. Binding of glycine to its receptor enhances the NMDA receptor activation. Such NMDA receptor activation may be beneficial for the treatment of schizophrenia and other diseases linked to NMDA receptor dysfunction. An activation can be achieved by an inhibitor of the glycine transporter.

Molecular cloning has revealed the existence of two types of glycine transporters, GlyT-1 and GlyT-2, wherein GlyT-1 can be further subdivided into GlyT-1a, GlyT-1b and GlyT-1c.

The NMDA receptor is blocked by compounds such as phencyclidine which induce a psychotic state which resembles schizophrenia. Likewise, the NMDA antagonists, such as ketamine, induce negative and cognitive symptoms similar to schizophrenia. This indicates that NMDA receptor dysfunction is involved in the pathophysiology of schizophrenia.

The NMDA receptor has been associated with a number of diseases, such as pain (Yaksh *Pain* 1989, 37, 111-123), spasticity, myuoclonus and epilepsy (Truong et. al. *Movement Disorders* 1988, 3, 77-87), learning and memory (Rison et. al. *Neurosci. Biobehav. Rev.* 1995, 19, 533-552), post-traumatic stress disorder (abbreviated: PTSD) (Heresco-levy et. al. *The International Journal of Neuropsychopharmacology*, 2002, 5:301-307, entitled: "Pilot-controlled trial of D-cycloserine for the treatment of post-traumatic stress disorder").

Glycine transporter antagonists or inhibiters are believed to be highly beneficial in the treatment of schizophrenia (Javitt WO 97/20553).

Glycine transport antagonists or inhibiters could be useful for the treatment of both the positive and the negative symptoms of schizophrenia and other psychoses, and in the improvement of cognition in conditions where the cognitive processes are diminished, i.e. Alzheimer's disease, multi-infarct dementia, ADDS dementia, Huntington's disease, Parkinson's disease, amyotrophic lateral sclerosis or diseases wherein the brain is damaged by inner or outer influence, such as trauma to the head or stroke. Likewise, convulsive disorders such as epilepsy, spasticity or myoclonus may benefit from glycine transporter antagonists.

Clinical trials with glycine have been reported, Javitt et. al. *Am. J. Psychiatry* 1994, 151, 1234-1236 and Leiderman et. al. *Biol. Psychiatry* 1996, 39, 213-215. The treatment with high-dose glycine is reported to improve the symptoms of schizophrenia. There is a need for more efficient compounds for the treatment of NMDA associated diseases.

SUMMARY OF THE INVENTION

The present invention relates to compounds of formula I which are potent inhibiters of the glycine transport. In one aspect, the present invention relates to a compound of the general formula I

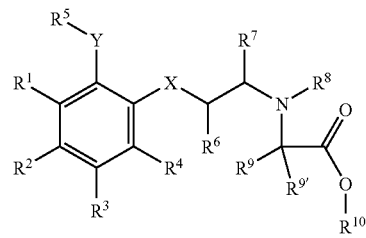

wherein the substituents are as defined below.

Furthermore, the invention provides a compound of formula I as above for use as a medicament.

Moreover, the invention provides a pharmaceutical composition comprising a compound of formula I as above or a pharmaceutically acceptable salt thereof, e.g. a pharmaceutically acceptable acid addition salt thereof, and at least one pharmaceutically acceptable carrier or diluent.

The invention also provides the use of a compound of formula I as above or a pharmaceutically acceptable acid addition salt thereof for the preparation of a medicament for the treatment of diseases selected from the group consisting of schizophrenia, including both the positive and the negative symptoms of schizophrenia and other psychoses, and in the improvement of cognition in conditions where the cognitive processes are diminished, i.e. Alzheimer's disease, multi-infarct dementia, AIDS dementia, Huntington's disease, Parkinson's disease, amyotrophic lateral sclerosis or diseases wherein the brain is damaged by inner or outer influence, such as trauma to the head or stroke, and convulsive disorders such as epilepsy, spasticity or myoclonus.

The invention also provides the use of a compound of formula I as above or a pharmaceutically acceptable acid addition salt thereof for the preparation of a medicament for the treatment of post-traumatic stress disorder.

The invention also provides a method for the treatment of diseases selected from the group consisting of schizophrenia, including both the positive and the negative symptoms of schizophrenia and other psychoses, and in the improvement of cognition in conditions where the cognitive processes are diminished, i.e. Alzheimer's disease, multi-infarct dementia, AIDS dementia, Huntington's disease, Parkinson's disease, amyotrophic lateral sclerosis or diseases wherein the brain is damaged by inner or outer influence, such as trauma to the head or stroke, and convulsive disorders such as epilepsy, spasticity or myoclonus in a living animal body, including a human, comprising administering a therapeutically effective amount of a compound of formula I as above or a pharmaceutically acceptable acid addition salt thereof.

The invention also provides a method for the treatment of post-traumatic stress disorder in a living animal body, including a human, comprising administering a therapeutically effective amount of a compound of formula I as above or a pharmaceutically acceptable acid addition salt thereof.

Definitions

The term "halogen" means fluoro, chloro, bromo or iodo.

The expression "$C_{1-6}$-alk(en/yn)yl" means a $C_{1-6}$-alkyl, $C_{2-6}$-alkenyl or a $C_{2-6}$-alkynyl group. The expression "$C_{3-8}$-cycloalk(en)yl" means a $C_{3-8}$-cycloalkyl- or cycloalkenyl group.

The term "$C_{1-6}$ alkyl" refers to a branched or unbranched alkyl group having from one to six carbon atoms inclusive, including but not limited to methyl, ethyl, 1-propyl, 2-propyl, 1-butyl, 2-butyl, 2-methyl-2-propyl and 2-methyl-1-propyl.

The term "$C_{2-6}$ alkenyl" designate such groups having from two to six carbon atoms, including one double bond, including but not limited to ethenyl, propenyl, and butenyl.

The term "$C_{2-6}$ alkynyl" designate such groups having from two to six carbon atoms, including one triple bond, including but not limited to ethynyl, propynyl and butynyl.

The term "$C_{3-8}$ cycloalkyl" designates a monocyclic or bicyclic carbocycle having three to eight C-atoms, including but not limited to cyclopropyl, cyclopentyl, cyclohexyl, etc.

The term "$C_{3-8}$ cycloalkenyl" designates a monocyclic or bicyclic carbocycle having three to eight C-atoms and including one double bond.

In the term "$C_{3-8}$-cycloalk(en)yl-$C_{1-6}$-alk(en/yn)yl", $C_{3-8}$-cycloalk(en)yl and $C_{1-6}$-alk(en/yn)yl are as defined above.

The terms "$C_{1-6}$-alc(en/yn)yloxy", "$C_{1-6}$ alk(en/yn)ylsulfanyl", "hydroxy-$C_{1-6}$-alk(en/yn)yl", "halo-$C_{1-6}$-alk(en/yn)yl", "halo-$C_{1-6}$-alk(en/yn)yloxy", "$C_{1-6}$-alk(en/yn)ylsulfonyl" etc. designate such groups in which the $C_{1-6}$-alk(en/yn)yl is as defined above, and "halo" means halogen.

The term "$C_{1-6}$ alk(en/yn)ylsulfanyl-$C_{1-6}$-alk(en/yn)yl" designate such group in which the $C_{1-6}$ alk(en/yn)ylsulfanyl and $C_{1-6}$-alk(en/yn)yl are as defined above.

As used herein, the term "$C_{1-6}$-alk(en/yn)yloxycarbonyl" refers to groups of the formula $C_{1-6}$-alk(en/yn)yl-O—CO—, wherein $C_{1-6}$-alk(en/yn)yl are as defined above.

As used herein, the term "acyl" refers to formyl, $C_{1-6}$-alk(en/yn)ylcarbonyl, arylcarbonyl, aryl-$C_{1-6}$-alk(en/yn)ylcarbonyl, $C_{3-8}$-cycloalk(en)ylcarbonyl or a $C_{3-8}$-cycloalk(en)yl-$C_{1-6}$-alk(en/yn)yl-carbonyl group, wherein aryl is defined below.

The term "together with the nitrogen form a saturated 3-7-membered heterocyclic ring" as used herein refers to saturated ring systems having from 2 to 6 carbon atoms and one nitrogen, such as 1-pyrrolidinyl, 1-piperidinyl or 1-azepinyl, all of which may be further substituted with $C_{1-6}$-alkyl.

The term "together with the nitrogen form a 3-7-membered heterocyclic ring which optionally contains one further heteroatom selected from O, S, or N" as used herein refers to saturated or unsaturated ring systems having from 2 to 6 carbon atoms and one nitrogen, or 2 to 5 carbon atoms and two nitrogens, one nitrogen and one oxygen, or one nitrogen and one sulphur, such as 1-morpholinyl, 1-piperidinyl, 1-pyrrolidinyl, 1-azepinyl, 1-piperazinyl, 1-homopiperazinyl, 1-imidazolyl, 1-pyrrolyl or 1-pyrazolyl, all of which may be further substituted with $C_{1-6}$-alkyl.

The term "aryl" refers to carbocyclic, aromatic systems, such as phenyl and naphthyl.

The term "monocyclic heteroaryl" refers to 5- to 6-membered aromatic systems containing 1 to 5 carbon atoms and one or more heteroatoms selected from O, S or N, such as 5-membered monocyclic rings such as oxathiazoles, dioxazoles, dithiazoles, oxadiazoles, thiadiazoles, triazoles, isoxazoles, oxazoles, isothiazoles, thiazoles, imidazoles, pyrazoles, pyrroles, furan(s) or thiophene(s), e.g. 3H-1,2,3-oxathiazole, 1,3,2-oxathiazole, 1,3,2-dioxazole, 3H-1,2,3-dithiazole, 1,3,2-dithiazole, 1,2,3-oxadiazole, 1,2,3-thiadiazole, 1H-1,2,3-triazole, isoxazole, oxazole, isothiazole, thiazole, 1H-imidazole, 1H-pyrazole, 1H-pyrrole, furan or thiophene, or 6-membered monocyclic rings such as oxathiazines, dioxazines, dithiazines, oxadiazines, thiadiazines, triazines, oxazines, thiazines, pyrazines, pyridazines, pyrimidines, oxathiins, dioxins, dithiins, pyridines, pyrans or thiins, e.g. 1,2,3-oxathiazine, 1,2,4-oxathiazine, 1,2,5-oxathiazine, 1,4,2-oxathiazine, 1,4,3-oxathiazine, 1,2,3-dioxazine, 1,2,4-dioxazine, 4H-1,3,2-dioxazine, 1,4,2-dioxazine, 2H-1,5,2-dioxazine, 1,2,3-dithiazine, 1,2,4-dithiazine, 4H-1,3,2-dithiazine, 1,4,2-dithiazine, 2H-1,5,2-dithiazine, 2H-1,2,3-oxadiazine, 2H-1,2,4-oxadiazine, 2H-1,2,5-oxadiazine, 2H-1,2,6-oxadiazine, 2H-1,3,4-oxadiazine, 2H-1,2,3-thiadiazine, 2H-1,2,4-thiadiazine, 2H-1,2,5-thiadiazine, 2H-1,2,6-thiadiazine, 2H-1,3,4-thiadiazine, 1,2,3-triazine, 1,2,4-triazine, 2H-1,2-oxazine, 2H-1,3-oxazine, 2H-1,4-oxazine, 2H-1,2-thiazine, 2H-1,3-thiazine, 2H-1,4-thiazine, pyrazine, pyridazine, 1,3-pyrimidine, 4H-1,3-oxathiin, 1,4-oxathiin, 4H-1,3-dioxin, 1,4-dioxin, 4H-1,3-dithiin, 1,4-dithiin, pyridine, 2H-pyran or 2H-thiin.

The term "alkali metal" refers to lithium, sodium, potassium and cesium.

DESCRIPTION OF THE INVENTION

The present invention relates to compounds of formula I which are potent inhibiters of the glycine transporter and consequently they are useful in treating diseases associated with NMDA dysfunction, such as schizophrenia.

In one aspect, the present invention relates to a compound of the general formula I

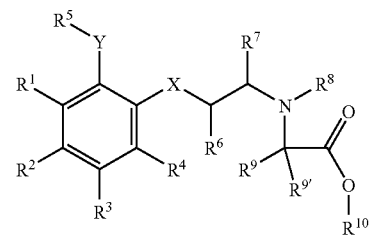

wherein

X is O, S or $CR^{11}R^{12}$, wherein $R^{11}$ and $R^{12}$ independently are selected from H or $C_{1-6}$ alkyl;

Y is O or S;

$R^1$, $R^2$, $R^3$ and $R^4$ are independently selected from hydrogen; halogen; cyano; nitro; $C_{1-6}$-alk(en/yn)yl; $C_{1-6}$-alk(en/yn)yloxy; $C_{1-6}$-alk(en/yn)ylsulfanyl; hydroxy; hydroxy-$C_{1-6}$-alk(en/yn)yl; halo-$C_{1-6}$-alk(en/yn)yl; halo-$C_{1-6}$-alk(en/yn)yloxy; $C_{3-8}$-cycloalk(en)yl; $C_{3-8}$-cycloalk(en)yl-$C_{1-6}$-alk(en/yn)yl; acyl; $C_{1-6}$-alk(en/yn)yloxycarbonyl; $C_{1-6}$-alk(en/yn)ylsulfonyl; aryl optionally substituted with a halogen, cyano, nitro, $C_{1-6}$-alk(en/yn)yl, $C_{1-6}$-alk(en/yn)yloxy, $C_{1-6}$-alk(en/yn)ylsulfanyl, hydroxy, hydroxy-$C_{1-6}$-alk(en/yn)yl, halo-$C_{1-6}$-alk(en/yn)yl, halo-$C_{1-6}$-alk(en/yn)yloxy, $C_{3-8}$-cycloalk(en)yl, $C_{3-8}$-cycloalk(en)yl-$C_{1-6}$-alk(en/yn)yl, acyl, $C_{1-6}$-alk(en/yn)yloxycarbonyl or $C_{1-6}$-alk(en/yn)ylsulfonyl; monocyclic heteroaryl optionally substituted with a halogen, cyano, nitro, $C_{1-6}$-alk(en/yn)yl, $C_{1-6}$-alk(en/yn)yloxy, $C_{1-6}$-alk(en/yn)ylsulfanyl, hydroxy, hydroxy-$C_{1-6}$-alk(en/yn)yl, halo-$C_{1-6}$-alk(en/yn)yl, halo- $C_{1-6}$-alk(en/yn)yloxy, $C_{3-8}$-cycloalk(en)yl, $C_3$-s-cycloalk(en)yl-$C_{1-6}$-alk(en/yn)yl, acyl, $C_{1-6}$-alk(en/yn)yloxycarbonyl or $C_{1-6}$-alk(en/yn)ylsulfonyl; or —$NR^{13}R^{14}$ wherein $R^{13}$ and $R^{14}$ independently are selected from hydrogen, $C_{1-6}$-alk(en/yn)yl, $C_{3-8}$-cycloalk(en)yl, $C_{3-8}$-cycloalk(en)yl-$C_{1-6}$ alk(en/yn)yl or aryl, or $R^{13}$ and $R^{14}$ together with the nitrogen form a 3-7-membered heterocyclic ring which optionally contains one further heteroatom selected from O, S or N;

$R^5$ is aryl or monocyclic heteroaryl, optionally substituted with a halogen, cyano, nitro, $C_{1-6}$-alk(en/yn)yl, $C_{1-6}$-alk(en/yn)yloxy, $C_{1-6}$-alk(en/yn)ylsulfanyl, hydroxy, hydroxy-$C_{1-6}$-alk(en/yn)yl, halo-$C_{1-6}$-alk(en/yn)yl, halo-$C_{1-6}$-alk(en/yn)yloxy, $C_{3-8}$-cycloalk(en)yl, $C_{3-8}$-cycloalk(en)yl-$C_{1-6}$-alk(en/yn)yl, acyl, $C_{1-6}$-alk(en/yn)yloxycarbonyl, $C_{1-6}$-alk(en/yn)ylsulfonyl, or —$NR^{15}R^{16}$ wherein $R^{15}$ and $R^{16}$ independently are selected from hydrogen, $C_{1-6}$-alk(en/yn)yl, $C_{3-8}$-cycloalk(en)yl, $C_{3-8}$-cycloalk(en)yl-$C_{1-6}$ alk(en/yn)yl or aryl, or $R^{15}$ and $R^{16}$ together with the nitrogen form a 3-7-membered heterocyclic ring which optionally contains one further heteroatom selected from O, S or N;

$R^6$ is selected from H, $C_{1-6}$-alk(en/yn)yl, $C_{1-6}$-alk(en/yn)yloxy, $C_{1-6}$-alk(en/yn)ylsulfanyl, or $C_{3-8}$-cycloalk(en)yl, provided that when $R^6$ is selected from $C_{1-6}$-alk(en/yn)yloxy, or $C_{1-6}$-alk(en/yn)ylsulfanyl then X is $CR^{11}R^{12}$, wherein $R^{11}$ and $R^{12}$ independently are selected from H or $C_{1-6}$ alkyl;

$R^7$ and $R^8$ are independently selected from H, $C_{1-6}$-alk(en/yn)yl or $C_{3-8}$-cycloalk(en)yl;

$R^9$ and $R^{9'}$ are independently selected from H, $C_{1-6}$-alk(en/yn)yl, hydroxy-$C_{1-6}$-alk(en/yn)yl, $C_{1-6}$-alk(en/yn)ylsulfanyl-$C_{1-6}$-alk(en/yn)yl or $C_{3-8}$-cycloalk(en)yl; or $R^6$ and $R^8$ together with the nitrogen form a saturated 3-7 membered heterocyclic ring, and $R^7$ is selected from H, $C_{1-6}$-alk(en/yn)yl, or $C_{3-8}$-cycloalk(en)yl, and $R^9$ and $R^{9'}$ are independently selected from H, $C_{1-6}$-alk(en/yn)yl, hydroxy-$C_{1-6}$-alk(en/yn)yl, $C_{1-6}$ alk(en/yn)ylsulfanyl-$C_{1-6}$-alk(en/yn)yl, or $C_{3-8}$-cycloalk(en)yl; or $R^7$ and $R^8$ together with the nitrogen form a saturated 3-7 membered heterocyclic ring, and $R^6$ is selected from H, $C_{1-6}$-alk(en/yn)yl, $C_{1-6}$-alk(en/yn)yloxy, $C_{1-6}$-alk(en/yn)ylsulfanyl, or $C_{3-8}$-cycloalk(en)yl, provided that when $R^6$ is selected from $C_{1-6}$-alk(en/yn)yloxy, or $C_{1-6}$-alk(en/yn)ylsulfanyl then X is $CR^{11}R^{12}$, wherein $R^{11}$ and $R^{12}$ independently are selected from H, or $C_{1-6}$ alkyl, and $R^9$ and $R^{9'}$ are independently selected from H, $C_{1-6}$-alk(en/yn)yl, hydroxy-$C_{1-6}$-alk(en/yn)yl, $C_{1-6}$ alk(en/yn)ylsulfanyl-$C_{1-6}$-alk(en/yn)yl or $C_{3-8}$-cycloalk(en)yl; or $R^8$ and $R^9$ together with the nitrogen form a saturated 3-7 membered heterocyclic ring, and $R^6$ is selected from H, $C_{1-6}$-alk(en/yn)yl, $C_{1-6}$-alk(en/yn)yloxy, $C_{1-6}$-alk(en/yn)ylsulfanyl, or $C_{3-8}$-cycloalk(en)yl, provided that when $R^6$ is selected from $C_{1-6}$-alk(en/yn)yloxy, or $C_{1-6}$-alk(en/yn)ylsulfanyl then X is $CR^{11}R^{12}$, wherein $R^{11}$ and $R^{12}$ independently are selected from H or $C_{1-6}$ alkyl, and $R^7$ is selected from H, $C_{1-6}$-alk(en/yn)yl, or $C_{3-8}$-cycloalk(en)yl, and $R^{9'}$ is selected from H, $C_{1-6}$-alk(en/yn)yl, hydroxy-$C_{1-6}$-alk(en/yn)yl, $C_{1-6}$ alk(en/yn)ylsulfanyl-$C_{1-6}$-alk(en/yn)yl or $C_{3-8}$-cycloalk(en)yl;

$R^{10}$ is H, $C_{1-6}$-alk(en/yn)yl, aryl, aryl-$C_{1-6}$-alk(en/yn)yl, wherein aryl is optionally substituted with a halogen, $CF_3$, $OCF_3$, CN, $NO_2$ or $C_{1-6}$-alk(en/yn)yl; or an alkali metal, such as sodium, potassium or lithium;

or a salt thereof, such as a pharmaceutically acceptable salt.

In an embodiment of formula I, X is O. In another embodiment of formula I, X is S. In a further embodiment, X is $CR^{11}R^{12}$, wherein $R^{11}$ and $R^{12}$ independently are selected from $C_{1-6}$ alkyl, such as methyl. In a further embodiment, X is $CHR^{11}$, wherein $R^{11}$ is selected from $C_{1-6}$ alkyl, such as methyl. In a further embodiment, X is $CH_2$.

In a further embodiment of formula I, Y is O. In a further embodiment, Y is S.

In a further embodiment of formula I, X is O and Y is S.

In a further embodiment of formula I, $R^1$ is hydrogen. In a further embodiment, $R^1$ is selected from $C_{1-6}$-alkyl, such as methyl, ethyl, n-propyl, isopropyl or t-butyl. In a further embodiment, $R^1$ is selected from a halogen, such as Cl, F, Br or I, e.g. Cl. In a further embodiment of formula I, $R^1$ is —$NR^{13}R^{14}$ wherein $R^{13}$ and $R^{14}$ independently are selected from hydrogen, $C_{1-6}$-alk(en/yn)yl, $C_{3-8}$-cycloalk(en)yl, $C_{3-8}$-cycloalk(en)yl-$C_{1-6}$ alk(en/yn)yl or aryl. In a further embodiment of formula I, $R^1$ is —$NR^{13}R^{14}$ wherein $R^{13}$ and $R^{14}$ together with the nitrogen form a 3-7-membered heterocyclic ring selected from 1-morpholinyl, 1-piperidinyl, 1-pyrrolidinyl, 1-azepinyl, 1-piperazinyl, 1-homopiperazinyl, 1-imidazolyl, 1-pyrrolyl or 1-pyrazolyl, optionally substituted with a $C_{1-6}$-alkyl. In a further embodiment of formula I, $R^1$ is phenyl optionally substituted with a halogen, cyano, nitro, $C_{1-6}$-alk(en/yn)yl, $C_{1-6}$-alk(en/yn)yloxy, $C_{1-6}$-alk(en/yn)ylsulfanyl, hydroxy, hydroxy-$C_{1-6}$-alk(en/yn)yl, halo-$C_{1-6}$-alk(en/yn)yl, halo-$C_{1-6}$-alk(en/yn)yloxy, $C_{3-8}$-cycloalk(en)yl, $C_{3-8}$-cycloalk(en)yl-$C_{1-6}$-alk(en/yn)yl, acyl, $C_{1-6}$-alk(en/yn)yloxycarbonyl or $C_{1-6}$-alk(en/yn)ylsulfonyl, such as phenyl substituted with one or two subtituents, typically one, selected from $C_{1-6}$-alkyl, or $C_{1-6}$-alkoxy, e.g. methoxy.

In a further embodiment of formula I, $R^2$ is hydrogen. In a further embodiment, $R^2$ is selected from $C_{1-6}$-alkyl, such as methyl, ethyl, n-propyl, isopropyl or t-butyl. In a further embodiment, $R^1$ is selected from a halogen, such as Cl, F, Br or I, e.g. Cl. In a further embodiment of formula I, $R^2$ is cyano. In a further embodiment of formula I, $R^2$ is —$NR^{13}R^{14}$ wherein $R^{13}$ and $R^{14}$ independently are selected from hydrogen, $C_{1-6}$-alk(en/yn)yl, $C_{3-8}$-cycloalk(en)yl, $C_{3-8}$-cycloalk(en)yl-$C_{1-6}$ alk(en/yn)yl or aryl. In a further embodiment of formula I, $R^2$ is —$NR^{13}R^{14}$ wherein $R^{13}$ and $R^{14}$ together with the nitrogen form a 3-7-membered heterocyclic ring selected from 1-morpholinyl, 1-piperidinyl, 1-pyrrolidinyl, 1-azepinyl, 1-piperazinyl, 1-homopiperazinyl, 1-imidazolyl, 1-pyrrolyl or 1-pyrazolyl, optionally substituted with a $C_{1-6}$-alkyl. In a further embodiment of formula I, $R^2$ is selected from 1-morpholinyl, or 1-piperidinyl. In a further embodiment of formula I, $R^2$ is phenyl. In a further embodiment of formula I, $R^2$ is phenyl substituted with a halogen, cyano, nitro, $C_{1-6}$-alk(en/yn)yl, $C_{1-6}$-alk(en/yn)yloxy, $C_{1-6}$-alk(en/yn)ylsulfanyl, hydroxy, hydroxy-$C_{1-6}$-alk(en/yn)yl, halo-$C_{1-6}$-alk(en/yn)yl, halo-$C_{1-6}$-alk(en/yn)yloxy, $C_{3-8}$-cycloalk(en)yl, $C_{3-8}$-cycloalk(en)yl-$C_{1-6}$-alk(en/yn)yl, acyl, $C_{1-6}$-alk(en/yn)yloxycarbonyl or $C_{1-6}$-alk(en/yn)ylsulfonyl, such as phenyl substituted with one or two subtituents, typically one, selected from $C_{1-6}$-alkyl or $C_{1-6}$-alkoxy, e.g. methoxy, or one selected from cyano or $C_{1-6}$-alkylsulfonyl, such as methanesulfonyl. In a further embodiment of formula I, $R^2$ is a monocyclic heteroaryl, such as pyrimidinyl.

In a further embodiment of formula I, $R^3$ is hydrogen. In a further embodiment, $R^3$ is selected from $C_{1-6}$-alkyl, such as methyl, ethyl, n-propyl, isopropyl or t-butyl. In a further embodiment, $R^3$ is selected from a halogen, such as Cl, F, Br or I, e.g. Cl. In a further embodiment of formula I, $R^3$ is —$NR^{13}R^{14}$ wherein $R^{13}$ and $R^{14}$ independently are selected from hydrogen, $C_{1-6}$-alk(en/yn)yl, $C_{3-8}$-cycloalk(en)yl, $C_{3-8}$-cycloalk(en)yl-$C_{1-6}$ alk(en/yn)yl or aryl. In a further embodiment of formula I, $R^3$ is $-NR^{13}R^{14}$ wherein $R^{13}$ and $R^{14}$ together with the nitrogen form a 3-7-membered heterocyclic ring selected from 1-morpholinyl, 1-piperidinyl, 1-pyrrolidinyl, 1-azepinyl, 1-piperazinyl, 1-homopiperazinyl, 1-imidazolyl, 1-pyrrolyl or 1-pyrazolyl, optionally substituted with a $C_{1-6}$-alkyl. In a further embodiment of formula I, $R^3$ is phenyl. In a further embodiment of formula I, $R^3$ is phenyl substituted with a halogen, cyano, nitro, $C_{1-6}$-alk(en/yn)yl, $C_{1-6}$-al&(en/yn)yloxy, $C_{1-6}$-alW(en/yn)ylsulfanyl, hydroxy, hydroxy-$C_{1-6}$-alk(en/yn)yl, halo-$C_{1-6}$-alk(en/yn)yl, halo-$C_{1-6}$-alk(en/yn)yloxy, $C_{3-8}$-cycloalk(en)yl, $C_{3-8}$-cycloalk(en)yl-$C_{1-6}$-alk(en/yn)yl, acyl, $C_{1-6}$-alk(en/yn)yloxycarbonyl or $C_{1-6}$-alk(en/yn)ylsulfonyl, such as phenyl substituted with one or two subtituents, typically one, selected from $C_{1-6}$-alkyl or $C_{1-6}$-alkoxy, e.g. methoxy, or one selected from cyano. In a further embodiment of formula I, $R^3$ is a monocyclic heteroaryl, such as thiophenyl.

In a further embodiment of formula I, $R^4$ is hydrogen. In a further embodiment, $R^4$ is selected from $C_{1-6}$-alkyl, such as methyl, ethyl, n-propyl, isopropyl or t-butyl. In a further embodiment, $R^4$ is selected from a halogen, such as Cl, F, Br or I. In a further embodiment of formula I, $R^4$ is $-NR^{13}R^{14}$ wherein $R^{13}$ and $R^{14}$ independently are selected from hydrogen, $C_{1-6}$-alk(en/yn)yl, $C_3$-g-cycloalk(en)yl, $C_{3-8}$-cycloalk(en)yl-$C_{1-6}$alk(en/yn)yl or aryl. In a further embodiment of formula I, $R^4$ is $-NR^{13}R^{14}$ wherein $R^{13}$ and $R^{14}$ together with the nitrogen form a 3-7-membered heterocyclic ring selected from 1-morpholinyl, 1-piperidinyl, 1-pyrrolidinyl, 1-azepinyl, 1-piperazinyl, 1-homopiperazinyl, 1-imidazolyl, 1-pyrrolyl or 1-pyrazolyl, optionally substituted with a $C_{1-6}$-alkyl. In a further embodiment of formula I $R^4$ is phenyl optionally substituted with a halogen, cyano, nitro, $C_{1-6}$-alk(en/yn)yl, Cl-alk(en/yn)yloxy, $C_{1-6}$-alk(en/yn)ylsulfanyl, hydroxy, hydroxy-$C_{1-6}$-alk(en/yn)yl, halo-$C_{1-6}$-alk(en/yn)yl, halo-$C_{1-6}$-alk(en/yn)yloxy, $C_{3-8}$-cycloalk(en)yl, $C_{3-8}$-cycloalk(en)yl-$C_{1-6}$-alk(en/yn)yl, acyl, $C_{1-6}$-alk(en/yn)yloxycarbonyl or $C_{1-6}$-alk(en/yn)ylsulfonyl, such as phenyl substituted with one or two subtituents, typically one, selected from $C_{1-6}$-alkyl or $C_{1-6}$-alkoxy, e.g. methoxy.

In a further embodiment of formula I, $R^5$ is phenyl. In a further embodiment, $R^5$ is phenyl substituted with a halogen, $C_{1-6}$-alkyl, $C_{1-6}$-alkyloxy, $C_{1-6}$-alkylsulfanyl, halo-$C_{1-6}$-alkyl. The phenyl ring may contain 1, 2, 3, 4 or 5 substituents, typically 1 or 2 substituents independently selected from the above, such as Cl, F, methyl, t-butyl, methoxy, methylsulfanyl or $CF_3$. To illustrate this, without limiting the invention in any way, the following sub-structure of formula I is an embodiment of the invention:

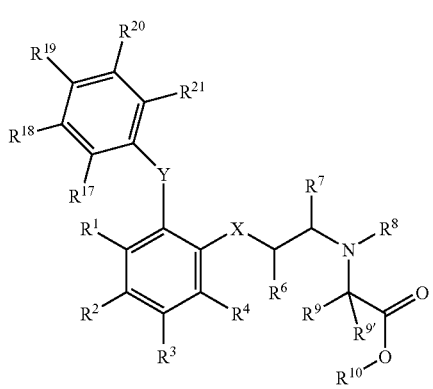

(Ia)

wherein $R^1$, $R^2$, $R^3$, $R^4$, $R^6$, $R^7$, $R^8$, $R^9$, $R^{9'}$, $R^{10}$, X and Y are as defined in formula I above, including the described embodiments above and below, and $R^{17}$, $R^{18}$, $R^{19}$, $R^{20}$ and $R^{21}$ are independently selected from H, halogen, $C_{1-6}$-alkyl, $C_{1-6}$-alkyloxy, $C_{1-6}$-alkylsulfanyl, halo-$C_{1-6}$-alkyl. In an embodiment $R^{17}$ is H. In an embodiment $R^{15}$ is selected from H; halogen, such as Cl, or F; halo-$C_{1-6}$-alkyl, such as $CF_3$; or $C_{1-6}$-alkyl, such as methyl. In an embodiment $R^{19}$ is selected from H; halogen, such as Cl, or F; halo-$C_{1-6}$-alkyl, such as $CF_3$; $C_{1-6}$-alkyl, such as methyl, or t-butyl; $C_{1-6}$-alkylsulfanyl, such as $-CH_3$; or $C_{1-4}$-alkyloxy, such as methoxy. In an embodiment, $R^{20}$ is selected from H; halogen, such as Cl or F; halo-$C_{1-6}$-alkyl, such as $CF_3$; or $C_{1-6}$-alkyl, such as methyl. In an embodiment $R^{21}$ is H. Typically, $R^{17}$ and $R^{21}$ are both H, and one or two of $R^{18}$, $R^{19}$ and $R^{20}$ is H, and the remaining substituent(s) is as defined above. In a further embodiment, $R^{17}$, $R^{19}$ and $R^{21}$ are all H, and one of $R^1$, and $R^{20}$ is halogen, such as F, and the other is hydrogen.

In a further embodiment of formula I, $R^5$ is naphthyl, such as 1-naphthyl, or 2-naphthyl. In a further embodiment, $R^5$ is naphthyl substituted with a halogen, $C_{1-6}$-alkyl, $C_{1-6}$-alkyloxy, $C_{1-6}$-alkylsulfanyl, halo-$C_{1-6}$-alkyl. The naphthyl may contain 1, 2, 3, 4 or 5 substituents, typically 1 or 2 substituents independently selected from the above, such as Cl, F, methyl, t-butyl, methoxy, methylsulfanyl or $CF_3$.

In a further embodiment of formula I, $R^5$ is monocyclic heteroaryl, optionally substituted with a halogen, cyano, nitro, $C_{1-6}$-alk(en/yn)yl, $C_{1-6}$-alk(en/yn)yloxy, $C_{1-6}$-alk(en/yn)ylsulfanyl, hydroxy, hydroxy-$C_{1-6}$-alk(en/yn)yl, halo-$C_{1-6}$-alk(en/yn)yl, halo-$C_{1-6}$-alk(en/yn)yloxy, $C_{3-8}$-cycloalk(en)yl, $C_{3-8}$-cycloalk(en)yl-$C_{1-6}$-alk(en/yn)yl, acyl, $C_{1-6}$-alk(en/yn)yloxycarbonyl, $C_{1-6}$-alk(en/yn)ylsulfonyl or $-NR^{15}R^{16}$ wherein $R^{15}$ and $R^{16}$ independently are selected from hydrogen, $C_{1-6}$-alk(en/yn)yl, $C_{3-8}$-cycloalk(en)yl, $C_{3-8}$-cycloalk(en)yl-$C_{1-6}$ alk(en/yn)yl or aryl, or $R^{15}$ and $R^{16}$ together with the nitrogen form a 3-7-membered heterocyclic ring which optionally contains one further heteroatom selected from O, S or N. Typically such monocyclic heteroaryl is selected from oxathiazoles, dioxazoles, dithiazoles, oxadiazoles, thiadiazoles, triazoles, isoxazoles, oxazoles, isothiazoles, thiazoles, imidazoles, pyrazoles, pyrroles, furan(s), thiophene(s), oxathiazines, dioxazines, dithiazines, oxadiazines, thiadiazines, triazines, oxazines, thiazines, pyrazines, pyridazines, pyrimidines, oxathiins, dioxins, dithiins, pyridines, pyrans or thins.

In a further embodiment of formula I, $R^6$ is H. In a further embodiment, $R^6$ is $C_{1-6}$-alkyl, such as methyl. In a further embodiment of formula I, $R^6$ is $C_{1-6}$-alk(en/yn)yloxy, such as $C_{1-6}$-alkyloxy, e.g. methoxy, provided that X is $CR^{11}R^{12}$, wherein $R^{11}$ and $R^{12}$ independently are selected from H, or $C_{1-6}$ alkyl. In a further embodiment of formula I, $R^6$ is $C_{1-6}$-alk(en/yn)ylsulfanyl, such as $C_{1-6}$-alkylsulfanyl, e.g. methylsulfanyl, provided that X is $CR^{11}R^{12}$, wherein $R^{11}$ and $R^{12}$ independently are selected from H or $C_{1-6}$ alkyl.

In a further embodiment of formula I, $R^7$ is H. In a further embodiment $R^7$ is $C_{1-6}$-alkyl, such as methyl, ethyl or isopropyl. In a further embodiment, $R^7$ is $C_{3-8}$-cycloalk(en)yl, such as $C_{3-8}$-cycloalkyl, e.g. cyclopropyl, cyclopentyl or cyclohexyl.

In a further embodiment of formula I, $R^8$ is H. In a further embodiment $R^8$ is $C_{1-6}$-alkyl, such as methyl, ethyl or isopropyl. In a further embodiment, $R^8$ is $C_{3-8}$-cycloalk(en)yl, such as $C_{3-8}$-cycloalkyl, e.g. cyclopropyl, cyclopentyl or cyclohexyl.

In a further embodiment of formula I, $R^9$ is H. In a further embodiment, $R^9$ is $C_{1-6}$-alkyl, such as methyl, ethyl or isopropyl. In a further embodiment, $R^9$ is hydroxy-$C_{1-6}$-alk(en/ yn)yl, such as hydroxy-$C_{1-6}$-alkyl, e.g. hydroxymethyl. In a further embodiment, $R^9$ is $C_{1-6}$ alk(en/yn)ylsulfanyl-$C_{1-6}$-alk(en/yn)yl, such as $C_{1-6}$ alkylsulfanyl-$C_{1-6}$-alkyl, e.g. methylsulfanylethyl.

In a further embodiment of formula I, $R^{9'}$ is H. In a further embodiment, $R^{9'}$ is $C_{1-6}$-alkyl, such as methyl, ethyl or isopropyl. In a further embodiment, $R^{9'}$ is hydroxy-$C_{1-6}$-alk(en/yn)yl, such as hydroxy-$C_{1-6}$-alkyl, e.g. hydroxymethyl. In a further embodiment, $R^{9'}$ is $C_{1-6}$ alk(en/yn)ylsulfanyl-$C_{1-6}$-alk(en/yn)yl, such as $C_{1-6}$ alkylsulfanyl-$C_{1-6}$-alkyl, e.g. methylsulfanylethyl.

Typically, one of $R^9$ and $R^{9'}$ is a hydrogen, however, they may both be independently selected from $C_{1-6}$-alkyl, such as methyl, ethyl or isopropyl; hydroxy-$C_{1-6}$-alk(en/yn)yl, such as hydroxy-$C_{1-6}$-alkyl; or $C_{1-6}$ alk(en/yn)ylsulfanyl-$C_{1-6}$-alk(en/yn)yl, such as $C_{1-6}$ alkylsulfanyl-$C_{1-6}$-alkyl.

In a further embodiment of formula I, $R^{10}$ is H.

In a further embodiment of formula I, $R^6$ and $R^8$ together with the nitrogen form a saturated 3-7 membered heterocyclic ring, and $R^7$ is selected from H, $C_{1-6}$-alk(en/yn)yl or $C_{3-8}$-cycloalk(en)yl, and $R^9$ and $R^{9'}$ are independently selected from H, $C_{1-6}$-alk(en/yn)yl, hydroxy-$C_{1-6}$-alk(en/yn)yl, $C_{1-6}$ alk(en/yn)ylsulfanyl-$C_{1-6}$-alk(en/yn)yl or $C_{3-8}$-cycloalk(en)yl. To illustrate this, without limiting the invention in any way, the following sub-structures of formula I are independent embodiments of the invention:

(Ib)

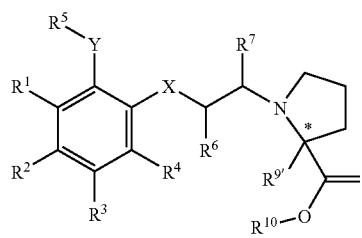

(Ic)

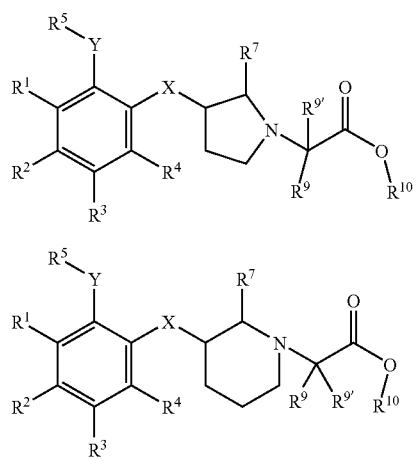

wherein $R^1$, $R^2$, $R^3$, $R^4$, $R^5$, $R^7$, $R^9$, $R^{9'}$, $R^{10}$, X and Y are as defined in formula I above, including the described embodiments.

In a further embodiment of formula I, $R^7$ and $R^8$ together with the nitrogen form a saturated 3-7 membered heterocyclic ring, and $R^6$ is selected from H, $C_{1-6}$-alk(en/yn)yl, $C_{1-6}$-alk(en/yn)yloxy, $C_{1-6}$-alk(en/yn)ylsulfanyl or $C_{3-8}$-cycloalk(en)yl, provided that when $R^6$ is selected from $C_{1-6}$-alk(en/yn)yloxy or $C_{1-6}$-alk(en/yn)ylsulfanyl then X is $CR^{11}R^{12}$, wherein $R^{11}$ and $R^{12}$ independently are selected from H or $C_{1-6}$ alkyl, and $R^9$ and $R^{9'}$ are independently selected from H, $C_{1-6}$-alk(en/yn)yl, hydroxy-$C_{1-6}$-alk(en/yn)yl, $C_{1-6}$ alk(en/yn)ylsulfanyl-$C_{1-6}$-alk(en/yn)yl or $C_{3-8}$-cycloalk(en)yl. To illustrate this, without limiting the invention in any way, the following sub-structure of formula I is an embodiment of the invention:

(Id)

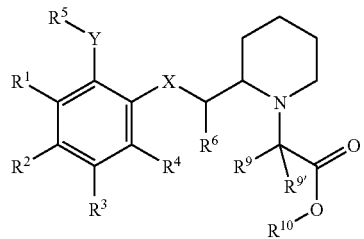

wherein $R^1$, $R^2$, $R^3$, $R^4$, $R^5$, $R^6$, $R^9$, $R^{9'}$, $R^{10}$, X and Y are as defined in formula I above, including the described embodiments.

In a farther embodiment of formula I, $R^8$ and $R^9$ together with the nitrogen form a saturated 3-7 membered heterocyclic ring, and $R^6$ is selected from H, $C_{1-6}$-alk(en/yn)yl, $C_{1-6}$-alk(en/yn)yloxy, $C_{1-6}$-alk(en/yn)ylsulfanyl or $C_{3-8}$-cycloalk(en)yl, provided that when $R^6$ is selected from $C_{1-6}$-alk(en/yn)yloxy or $C_{1-6}$-alk(en/yn)ylsulfanyl then X is $CR^{11}R^{12}$, wherein $R^{11}$ and $R^{12}$ independently are selected from H or $C_{1-6}$ alkyl, and $R^7$ is selected from H, $C_{1-6}$-alk(en/yn)yl or $C_{3-8}$-cycloalk(en)yl, and $R^{9'}$ is selected from H, $C_{1-6}$-alk(en/yn)yl, hydroxy-$C_{1-6}$-alk(en/yn)yl, $C_{1-6}$ alk(en/yn)ylsulfanyl-$C_{1-6}$-alk(en/yn)yl or $C_{3-8}$-cycloalk(en)yl. To illustrate this, without limiting the invention in any way, the following sub-structure of formula I is an embodiment of the invention:

(Ie)

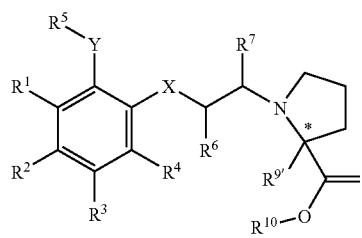

wherein $R^1$, $R^2$, $R^3$, $R^4$, $R^5$, $R^6$, $R^7$, $R^{9'}$, $R^{10}$, X and Y are as defined in formula I above, including the described embodiments, and the asterix means that the carbon atom whereto $R^{9'}$ is attached is a chiral center. In one embodiment of formula Ie, the * designates a racemic mixture of the R- and S-isomer. In a farther embodiment of formula Ie, the * designates the R-isomer. In a further embodiment of formula Ie, the * designates the S-isomer.

In further embodiments of formula I, the compound is any one of
(S)-1-{2-[2-(4-Fluoro-phenylsulfanyl)-phenoxy]-ethyl}-pyrrolidine-2-carboxylic acid,
(S)-1-{2-[2-(4-tert-Butyl-phenylsulfanyl)-phenoxy]-ethyl}-pyrrolidine-2-carboxylic acid,
(S)-1-{2-[2-(4-Trifluoromethyl-phenylsulfanyl)-phenoxy]-ethyl}-pyrrolidine-2-carboxylic acid,
(S)-1-{2-[2-(3-Fluoro-phenylsulfanyl)-phenoxy]-ethyl}-pyrrolidine-2-carboxylic acid,
(S)-{2-[2-(4-Chloro-phenylsulfanyl)-phenoxy]-ethyl}-pyrrolidine-2-carboxylic acid,
(S)-1-{2-[2-(3-Chloro-phenylsulfanyl)-phenoxy]-ethyl}-pyrrolidine-2-carboxylic acid,
(S)-1-{2-[2-(3,4-Dichloro-phenylsulfanyl)-phenoxy]-ethyl}-pyrrolidine-2-carboxylic acid, (S)-1-{2-[2-(3-Chloro-4-fluoro-phenylsulfanyl)-phenoxy]-ethyl}-pyrrolidine-2-carboxylic acid,
(S)-1-{2-[2-(3-Chloro-phenoxy)-phenoxy]-ethyl}-pyrrolidine-2-carboxylic acid,
(S)-1-{2-[2-(4-Chloro-phenoxy)-phenoxy]-ethyl}-pyrrolidine-2-carboxylic acid,
(S)-1-{2-[2-(4-Methoxy-phenoxy)-phenoxy]-ethyl}-pyrrolidine-2-carboxylic acid,
(S)-1-{2-[2-(3,4-Difluoro-phenoxy)-phenoxy]-ethyl}-pyrrolidine-2-carboxylic acid,
1-{2(R/S)-[2-(4-Chloro-phenoxy)-phenoxy]-propyl}-pyrrolidine-2(S)-carboxylic acid,
1-{2(R/S)-[2-(3,4-Difluoro-phenoxy)-phenoxy]-propyl}-pyrrolidine-2(S)-carboxylic acid,
(S)-1-{2-[2-(3-Fluoro-phenoxy)-phenoxy]-ethyl}-pyrrolidine-2-carboxylic acid,
1-{2(R/S)-[2-(3-Fluoro-phenoxy)-phenoxy]-propyl}-pyrrolidine-2(S)-carboxylic acid,
1-{2(R/S)-[2-(3-Fluoro-phenylsulfanyl)-phenoxy]-propyl}-pyrrolidine-2(S)-carboxylic acid,
1-{2(R/S)-[2-(3-Chloro-phenylsulfanyl)-phenoxy]-propyl}-pyrrolidine-2(S)-carboxylic acid,
({2-[2-(4-tert-Butyl-phenylsulfanyl)-phenoxy]-ethyl}-N-ethyl-amino)-acetic acid,
2-{3-[2-(4-tert-Butyl-phenylsulfanyl)-phenoxy]-pyrrolidin-1-yl}-propionic acid,
({2-[2-(3-Chloro-phenylsulfanyl)-phenoxy]-ethyl}-N-methyl-amino)-acetic acid,
({2-[2-(3-Chloro-4-fluoro-phenylsulfanyl)-phenoxy]-ethyl}-N-methyl-amino)-acetic acid,
{2-[2-(4-tert-Butyl-phenylsulfanyl)-phenoxymethyl]-piperidin-1-yl}-acetic acid,
({2-[2-(3-Fluoro-phenylsulfanyl)-phenoxy]-ethyl}-N-methyl-amino)-acetic acid,
{4-[2-(4-tert-Butyl-phenylsulfanyl)-phenoxy]-piperidin-1-yl}-acetic acid,
(N-2-propyl-{2-[2-(4-trifluoromethyl-phenylsulfanyl)-phenoxy]-ethyl}-amino)-acetic acid,
({2-[2-(3,4-Dichloro-phenylsulfanyl)-phenoxy]-ethyl}-N-ethyl-amino)-acetic acid,
(N-Ethyl-{2-[2-(4-methylsulfanyl-phenylsulfanyl)-phenoxy]-ethyl}-amino)-acetic acid,
2-{3-[2-(3,4-Dichloro-phenylsulfanyl)-phenoxy]-pyrrolidin-1-yl}-propionic acid,
(S)-{3-[2-(4-tert-Butyl-phenylsulfanyl)-phenoxy]-pyrrolidin-1-yl}-acetic acid,
({2-[2-(3-Chloro-4-fluoro-phenylsulfanyl)-phenoxy]-ethyl}-N-ethyl-amino)-acetic acid,
(N-2-propyl-{2-[2-(4-methylsulfanyl-phenylsulfanyl)-phenoxy]-ethyl}-amino)-acetic acid,
{3-[2-(4-tert-Butyl-phenylsulfanyl)-phenoxy]-pyrrolidin-1-yl}-acetic acid,
({2-[2-(3-Chloro-phenylsulfanyl)-phenoxy]-ethyl}-N-ethyl-amino)-acetic acid,
({2-[2-(4-Chloro-phenylsulfanyl)-phenoxy]-ethyl-}N-methyl-amino)-acetic acid,
{4-[2-(3,4-Dichloro-phenylsulfanyl)-phenoxy]-piperidin-1-yl}-acetic acid,
2-{3-[2-(4-Trifluoromethyl-phenylsulfanyl)-phenoxy]-pyrrolidin-1-yl}-propionic acid,
({2-[2-(4-tert-Butyl-phenylsulfanyl)-phenoxy]-ethyl}-N-2-propyl-amino)-acetic acid
({2-[2-(4-tert-Butyl-phenylsulfanyl)-phenoxy]-ethyl}-N-methyl-amino)-acetic acid,
{2-[2-(4-Methylsulfanyl-phenylsulfanyl)-phenoxymethyl]-piperidin-1-yl}-acetic acid,
({2-[2-(3,4-Dichloro-phenylsulfanyl)-phenoxy]-ethyl}-N-methyl-amino)-acetic acid,
(N-Methyl-{2-[2-(4-trifluoromethyl-phenylsulfanyl)-phenoxy]-ethyl}-amino)-acetic acid,
2-{3(R)-[2-(4-tert-Butyl-phenylsulfanyl)-phenoxy]-pyrrolidin-1-yl}-propionic acid,
2-{3(R)-[2-(3,4-Dichloro-phenylsulfanyl)-phenoxy]-pyrrolidin-1-yl}-propionic acid,
2-[3(R)-(2-(4-methylphenyl)-sulfanyl-phenoxy)-pyrrolidin-1-yl]-propionic acid,
{3(R)-[2-(4-tert-Butyl-phenylsulfanyl)-phenoxy]-pyrrolidin-1-yl}-acetic acid,
2-{3(R)-[2-(4-Trifluoromethyl-phenylsulfanyl)-phenoxy]-pyrrolidin-1-yl}-propionic acid,
2-{3(R)-[2-(4-Chloro-phenylsulfanyl)-phenoxy]-pyrrolidin-1-yl}-propionic acid,
({1-[2-(3-Chloro-phenylsulfanyl)-phenoxymethyl]-propyl}-N-ethyl-amino)-acetic acid,
({1-[2-(3,4-Dichloro-phenylsulfanyl)-phenoxy]-butan-2-yl}-N-ethyl-amino)-acetic acid,
({-[2-(3,4-Dichloro-phenylsulfanyl)-phenoxy]-butan-3-methyl-2-yl}-N-ethyl-amino)-acetic acid,
({1-[2-(3-Chloro-4-fluoro-phenylsulfanyl)-phenoxy]-butan-2-yl}-N-ethyl-amino)-acetic acid,
({1-[1-(3-Chloro-phenylsulfanyl)-phenoxy]-propan-2-yl}-N-ethyl-amino)-acetic acid,
({1-[2-(3-Chloro-4-fluoro-phenylsulfanyl)-phenoxy]-butan-3-methyl-2-yl}-N-ethyl-amino)-acetic acid,
({1-[2-(3-Chloro-4-fluoro-phenylsulfanyl)-phenoxy]propan-2-yl}-N-ethyl-amino)-acetic acid,
(S)-({1-[2-(3-Chloro-phenylsulfanyl)-phenoxy]-propan-2-yl}-N-methyl-amino)-acetic acid,
(S)-({1-[2-(3-Chloro-phenylsulfanyl)-phenoxy]-propan-2-yl}-N-ethyl-amino)-acetic acid,
({1-[2-(3,4-Dichloro-phenylsulfanyl)-phenoxy]-propan-2-yl}-N-ethyl-amino)-acetic acid,
({1-[2-(4-Chloro-phenylsulfanyl)-phenoxy]-propan-2-yl}-N-ethyl-amino)-acetic acid,
({1-[2-(3-Chloro-phenylsulfanyl)-phenoxymethyl]-propyl}-N-methyl-amino)-acetic acid,
({1-[2-(4-Chloro-phenylsulfanyl)-phenoxymethyl]-propyl}-N-ethyl-amino)-acetic acid,
(N-Ethyl-{1-[2-(3-fluoro-phenylsulfanyl)-phenoxymethyl]-propyl}-amino)-acetic acid,
(R)-({2-[2-(3,4-Dichloro-phenylsulfanyl)-phenoxy]-1-methyl-ethyl}-N-ethyl-amino)-acetic acid,
(S)-(2-{1-[2-(4-Chloro-phenoxy)-phenoxy]-propan-2-yl}-N-methyl-amino)-acetic acid,
(R)-(2-{1-[2-(3-Chloro-phenylsulfanyl)-phenoxy]-propan-2-yl}-N-methyl-amino)-acetic acid,
({2-[2-(3-Fluoro-phenylsulfanyl)-phenoxy]-propyl}-N-methyl-amino)-acetic acid,
({2-[2-(3-Chloro-phenylsulfanyl)-phenoxy]-propan-1yl}-N-ethyl-amino)-acetic acid,
({1-[2-(3-Chloro-phenylsulfanyl)-phenoxy]-3-methyl-butan-2-yl}-N-methyl-amino)-acetic acid,
({3-methyl-1-[2-(4-trifluoromethyl-phenylsulfanyl)-phenoxy]-butan-2-yl}-N-ethyl-amino)-acetic acid,
({1-[2-(3-Chloro-4-fluoro-phenylsulfanyl)-phenoxy]-butan-2-yl}-N-methyl-amino)-acetic acid,
(S)-({1-[2-(3-Chloro-4-fluoro-phenylsulfanyl)-phenoxy]-propan-2-yl}N-methyl-amino)-acetic acid,
(S)-({1-[2-(3-Fluoro-phenylsulfanyl)-phenoxy]-propan2-yl}-N-methyl-amino)-acetic acid,
({1-[2-(4-tert-Butyl-phenylsulfanyl)-phenoxy]-3-methyl-butan-2-yl}-N-ethyl-amino)-acetic acid, (S)-({1-[2-(3,4-Dichloro-phenylsulfanyl)-phenoxy]-propan-2-yl}-N-methyl-amino)-acetic acid,
({1-[2-(3-Chloro-4-fluoro-phenylsulfanyl)-phenoxy]-3-methyl-butan-2-yl}-N-methyl-amino)-acetic acid,
({1-[2-(4-tert-Butyl-phenylsulfanyl)-phenoxy]-3-methyl-propan-2-yl}-N-ethyl-amino)-acetic acid,
({2-[2-(3-Chloro-4-fluoro-phenylsulfanyl)-phenoxy]-propan-1-yl}-N-ethyl-amino)-acetic acid,
({2-[2-(4-methoxy-phenylsulfanyl)-phenoxy]-propan-1-yl}-N-Cyclohexyl-amino)-acetic acid,
{[2-(2-(4-methylsulfanyl-phenoxy)-propan-1-yl-]-N-cyclohexyl-amino}-acetic acid,
({2-[2-(3-Chloro-phenylsulfanyl)-phenoxy]-propan-1-yl}-N-cyclohexyl-amino)-acetic acid,
(S)-1-{3-[2-(3-Fluoro-phenylsulfanyl)-phenyl]-propyl}-pyrrolidine-2-carboxylic acid,
(S)-2-({2-[3-(3-Fluoro-phenylsulfanyl)-biphenyl-4-yloxy]-ethyl}-methyl-amino)-propionic acid,
({2-[3-(3-Fluoro-phenylsulfanyl)-biphenyl-4-yloxy]-ethyl}-methyl-amino)-acetic acid,
(S)-1-{2-[4-Chloro-2-(3-fluoro-phenylsulfanyl)-phenoxy]-ethyl}-pyrrolidine-2-carboxylic acid,
(S)-1-{2-[3-Chloro-2-(3-fluoro-phenylsulfinyl)-phenoxy]-ethyl}pyrrolidine-2-carboxylic acid,
(S)-1-{2-[5-Chloro-2-(3-fluoro-phenylsulfanyl)-phenoxy]-ethyl}pyrrolidine-2-carboxylic acid,
(S)-1-{2-[4-Cyano-2-(3-fluoro-phenylsulfanyl)-phenoxy]-ethyl}-pyrrolidine-2-carboxylic acid
(S)-1-[2-(5-Chloro-2-phenylsulfanyl-phenoxy)-ethyl]pyrrolidine-2-carboxylic acid,
(S)-1-{2-[3-(3-Fluoro-phenylsulfanyl)-biphenyl-4-yloxy]-ethyl}-pyrrolidine-2-carboxylic acid,
(S)-{2-[4'-Methoxy-3-(3-fluoro-phenylsulfanyl)-biphenyl-4-yloxy]-ethyl}-pyrrolidine-2-carboxylic acid,
(S)-{2-[4'-Cyano-3-(3-fluoro-phenylsulfanyl)-biphenyl-4-yloxy]-ethyl}-pyrrolidine-2-carboxylic acid,
(S)-1-{2-[4'-Cyano-4-(3-fluoro-phenylsulfanyl)-biphenyl-3-yloxy]-ethyl}-pyrrolidine-2-carboxylic acid,
(S)-1-{2-[2-(3-Fluoro-phenylsulfanyl)-5-thiophen-3-yl-phenoxy]-ethyl}-pyrrolidine-2-carboxylic acid,
(S)-1-{2-[2-(3-Fluoro-phenylsulfanyl)-4-pyrimidin-5-yl-phenoxy]-ethyl}-pyrrolidine-2-carboxylic acid,
(S)-1-{2-[3-(3-Fluoro-phenylsulfanyl)-3-methanesulfonyl-biphenyl-4-yloxy]-ethyl}-pyrrolidine-2(S)-carboxylic acid,
(S)-1-{2-[2-(3-Fluoro-phenylsulfanyl)-4-morpholin-4-yl-phenoxy]-ethyl}-pyrrolidine-2-carboxylic acid,
(S)-1-{2-[2-(3-Fluoro-phenylsulfanyl)-4-piperidin-1-yl-phenoxy]-ethyl}-pyrrolidine-2-carboxylic acid,
or a pharmaceutically acceptable salt thereof. Each of these compounds is considered a specific embodiment and may be subject to individual claims.

The present invention also comprises salts of the present compounds, typically, pharmaceutically acceptable salts. Such salts include pharmaceutical acceptable acid addition salts, pharmaceutically acceptable metal salts, ammonium and alkylated ammonium salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in J. Pharm. Sci. 1977, 66, 2, which is incorporated herein by reference.

Examples of metal salts include lithium, sodium, potassium, magnesium salts and the like.

Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

The compounds of the present invention may have one or more asymmetric centres and it is intended that any optical isomers (i.e. enantiomers or diastereomers), as separated, pure or partially purified optical isomers and any mixtures thereof including racemic mixtures are included within the scope of the invention.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can also be resolved into their optical antipodes, e.g. by fractional crystallization of d- or l-(tartrates, mandelates or camphorsulphonate) salts. The compounds of the present invention may also be resolved by the formation of diastereomeric derivatives.

Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981).

Optically active compounds can also be prepared from optically active starting materials.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

The invention also encompasses prodrugs of the present compounds, which on administration undergo chemical conversion by metabolic processes before becoming pharmacologically active substances. In general, such prodrugs will be functional derivatives of the compounds of the general formula (I), which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

As mentioned above, the compounds of formula I are potent inhibiters of the glycine transporter, and accordingly may be applicable for the treatment, including prevention, of schizophrenia, including both the positive and the negative symptoms of schizophrenia and other psychoses, and in the improvement of cognition in conditions where the cognitive processes are diminished, i.e. Alzheimer's disease, multi-infarct dementia, AIDS dementia, Huntington's disease, Parkinson's disease, amyotrophic lateral sclerosis or diseases wherein the brain is damaged by inner or outer influence, such as trauma to the head or stroke, and convulsive disorders such as epilepsy, spasticity or myoclonus.

Accordingly, in a further aspect the invention relates to a compound of formula I for use as a medicament.

The present invention also relates to a pharmaceutical composition comprising a compound of formula I and a pharmaceutically acceptable carrier or diluent. The composition may comprise any one of the embodiments of formula I described above.

In an embodiment of the pharmaceutical composition, the compound of formula I is present in an amount of from about 0.001 to about 100 mg/kg body weight per day.

The present invention also relates to use of a compound of formula I for the preparation of a medicament for the treatment of a disease or disorder, wherein an inhibitor of the glycine transport is beneficial. The medicament may comprise any one of the embodiments of formula I described above.

In particular, the present invention also relates to use of a compound of formula I for the preparation of a medicament for the treatment of schizophrenia. Such schizophrenia includes both the positive and the negative symptoms of schizophrenia and other psychoses.

In a further embodiment, the present invention relates to use of a compound of formula I for the preparation of a medicament for the treatment of Alzheimer's disease. In a further embodiment, the present invention relates to use of a compound of formula I for the preparation of a medicament for the treatment of multi-infarct dementia. In a further embodiment, the present invention relates to use of a compound of formula I for the preparation of a medicament for the treatment of AIDS dementia. In a further embodiment, the present invention relates to use of a compound of formula I for the preparation of a medicament for the treatment of dementia. In a further embodiment, the present invention relates to use of a compound of formula I for the preparation of a medicament for the treatment of Huntington's disease. In a further embodiment, the present invention relates to use of a compound of formula I for the preparation of a medicament for the treatment of Parkinson's disease. In a further embodiment, the present invention relates to use of a compound of formula I for the preparation of a medicament for the treatment of amyotrophic lateral sclerosis. In a further embodiment, the present invention relates to use of a compound of formula I for the preparation of a medicament for the treatment of diseases wherein the brain is damaged by inner or outer influence. In a further embodiment, the present invention relates to use of a compound of formula I for the preparation of a medicament for the treatment of trauma to the head. In a further embodiment, the present invention relates to use of a compound of formula I for the preparation of a medicament for the treatment of stroke. In a further embodiment, the present invention relates to use of a compound of formula I for the preparation of a medicament for the treatment of convulsive disorders. In a further embodiment, the present invention relates to use of a compound of formula I for the preparation of a medicament for the treatment of epilepsy. In a further embodiment, the present invention relates to use of a compound of formula I for the preparation of a medicament for the treatment of spasticity. In a further embodiment, the present invention relates to use of a compound of formula I for the preparation of a medicament for the treatment of myoclonus. In a further embodiment, the present invention relates to the use of a compound of formula I as above or a pharmaceutically acceptable acid addition salt thereof for the preparation of a medicament for the treatment of post-traumatic stress disorder. The medicament may comprise any one of the embodiments of formula I described above.

A further aspect of the invention relates to a method for the treatment of a disease or disorder selected from the group consisting of the positive and the negative symptoms of schizophrenia, including both the positive and the negative symptoms of schizophrenia and other psychoses, and in the improvement of cognition in conditions where the cognitive processes are diminished, i.e. Alzheimer's disease, multi-infarct dementia, AIDS dementia, Huntington's disease, Parkinson's disease, amyotrophic lateral sclerosis or diseases wherein the brain is damaged by inner or outer influence, such as trauma to the head or stroke, and convulsive disorders such as epilepsy, spasticity or myoclonus, in a living animal body, including a human, comprising administering to a subject in need thereof a therapeutically effective amount of a compound of formula I.

A further aspect of the invention relates to a method for the treatment of post-traumatic stress disorder in a living animal body, including a human, comprising administering a therapeutically effective amount of a compound of formula I as above or a pharmaceutically acceptable acid addition salt thereof.

In a further aspect, the present invention relates to a method of preparing a compound of formula I, comprising coupling an alcohol of formula II

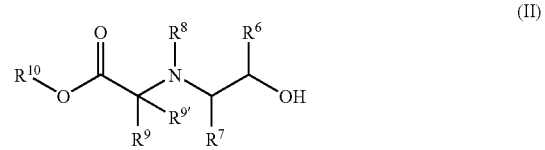

with a phenol of formula III

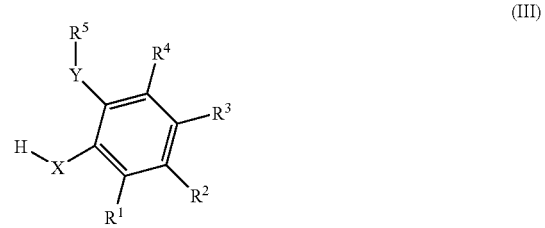

wherein $R^1$, $R^2$, $R^3$, $R^4$, $R^5$, $R^6$, $R^7$, $R^8$, $R^9$, $R^{9'}$, $R^{10}$, X and Y are as defined in formula I above.

The reaction is typically performed in a suitable solvent such as tetrahydrofuran or diethyl ether containing a coupling agent such as triphenylphosphine and diethylazodicarboxylate or 1,1'-(Azodicarbonyl)dipiperidine at room temperature.

Alternatively, the present invention relates to a method of preparing a compound of formula I, comprising alkylation of an amine of formula IV

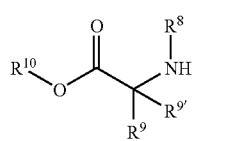

(IV)

with an alkylating agent of formula V

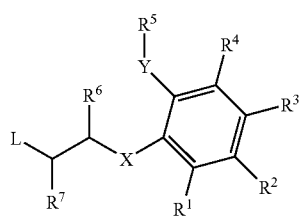

(V)

wherein $R^1$, $R^2$, $R^3$, $R^4$, $R^5$, $R^6$, $R^7$, $R^8$, $R^9$, $R^{9'}$, $R^{10}$, X and Y are as defined in formula I above, and L is a suitable leaving group such as halogen, mesylate or tosylate.

The reaction is typically performed in a suitable solvent such as ethanol, N,N-dimethylformamide or acetonitrile containing an inorganic base such as potassium or cesium carbonate or an organic base such N-ethyl diisopropylamine at an elevated temperature of 40-80° C.

Alternatively compounds of formula I may be prepared by coupling intermediates of of formula VI where Z is an iodide, $R^1$-$R^{10}$ are as described above and Y is sulfur.

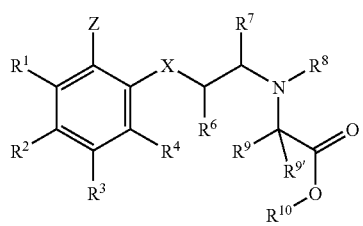

(VI)

with intermediates of formula VII

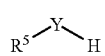

(VII)

The cross coupling reaction is typically performed as described by Schopfer (Tetrahedron, 2001, 57, 3069-3073) where an iodide of formula IV is coupled to a thiol of formula $R^5$—S—H using palladium catalysis in toluene at elevated temperatures.

Compounds of formula I wherein $R^{10}$ is hydrogen may be prepared by hydrolysis of the corresponding esters $COOR^{10}$ wherein $R^{10}$ is an insoluble polymer or e.g. $C_{1-6}$-alkyl, aryl or aryl-$C_{1-6}$-alkyl. This may be performed under basic conditions, for example, using aqueous sodium hydroxide in an alcoholic solvent or under acidic conditions in the hydrolysis of a tertiary-butyl ester or cleavage from an insoluble polymer. This, method is also an aspect of the present invention.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Depot injetable formulations are also contemplated as being within the scope of the present invention.

Other suitable administration forms include suppositories, sprays, ointments, creams, gels, inhalants, dermal patches, implants, etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.01 to about 1000 mg, preferably from about 0.05 to about 500 mg, and more preferred from about 0.5 mg to about 200 mg.

For parenteral routes such as intravenous, intrathecal, intramuscular and similar administration, typically doses are in the order of about half the dose employed for oral administration.

The compounds of this invention are generally utilized as the free substance or as a pharmaceutically acceptable salt thereof. One example is a base addition salt of a compound having the utility of a free acid. When a compound of the formula (I) contains a free acid such salts are prepared in a conventional manner by treating a solution or suspension of a free acid of the formula (I) with a chemical equivalent of a pharmaceutically acceptable base. Representative examples are mentioned above.

For parenteral administration, solutions of the novel compounds of the formula (I) in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospho lipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the novel compounds of the formula (I) and the pharmaceutical acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined. amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tablette, placed in a hard gelatine capsule in powder or pellet form or it can be in the form of a troche or lozenge.

The amount of solid carrier will vary widely but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

Method of Preparing the Compounds of Formula I

The compounds of the invention are prepared by the following general methods. Coupling of alcohol of formula II with a phenol of formula III

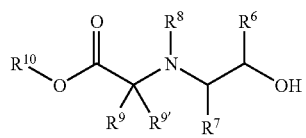

(II)

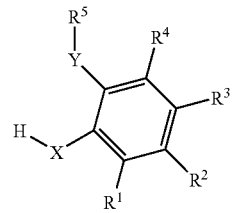

(III)

The substituents $R^1$-$R^{10}$ are as defined above, X is oxygen and Y is oxygen or sulfur. The reaction is typically performed in a suitable solvent such as tetrahydrofuran or diethyl ether containing a coupling agent such as a combination of a triaryl phosphine and diethylazodicarboxylate or 1,1'-(Azodicarbonyl)dipiperidine at room temperature as described by Mitsunobu (Synthesis, 1981, 1)

Alternatively compounds of the invention may be prepared by alkylation of amines of formula IV with alkylating agents of formula V.

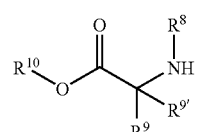

(IV)

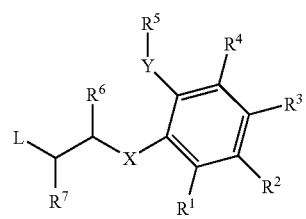

(V)

The substituents $R^1$-$R^{10}$, X and Y are as defined above. L is a suitable leaving group such as halogen, mesylate or tosylate. The reaction is typically performed in a suitable solvent such as ethanol, N,N-dimethylformamide or acetonitrile containing an inorganic base such as potassium or cesium carbonate or an organic base such N-ethyl diisopropylamine at an elevated temperature of 40-80° C.

Alternatively, compounds of the invention may be prepared by coupling intermediates of formula VI where Z is an iodide, $R^1$-$R^{10}$ are as described above and Y is sulfur.

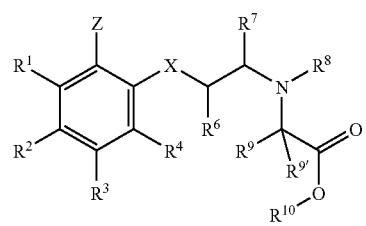

(VI)

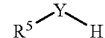

(VII)

The cross coupling reaction is typically performed as described by Schopfer (Tetrahedron, 2001, 57, 3069-3073) where an iodide of formula VI is coupled to a thiol of formula VII, $R^5$—S—H using palladium catalysis in toluene at elevated temperatures.

Compounds of formula I wherein $R^{10}$ is hydrogen may be prepared by hydrolysis of the corresponding esters $COOR^{10}$ wherein $R^{10}$ is an insoluble polymer or $C_{1-6}$-alkyl, aryl or aryl-$C_{1-6}$-alkyl. This may be performed under basic conditions, for example, using aqueous sodium hydroxide in an alcoholic solvent or under acidic conditions in the hydrolysis of a tertiary-butyl ester or cleavage from an insoluble polymer.

Compounds of formula II may be prepared as depicted in scheme 1.

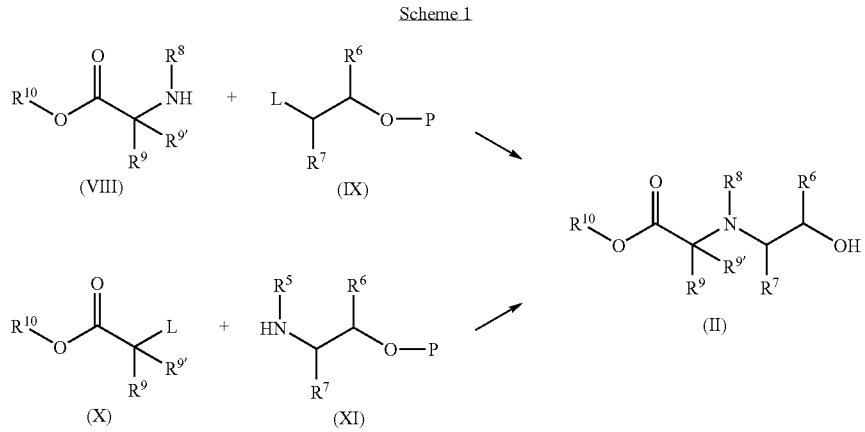

An amino acid derivative of formula VIII where $R^{10}$, $R^{9'}$, $R^9$ and $R^8$ are as defined above may be alkylated with an alkylating reagent of formula IX. Alternatively an acetic acid derivative of formula X where $R^{10}$, $R^{9'}$, $R^9$ are as defined above and L is a halogen, mesylate or tosylate may be reacted with an amine of formula XI where $R^5$, $R^6$ and $R^7$ are defined as above. The reaction is typically performed in a suitable solvent such as ethanol, N,N-dimethylformamide, DMSO or acetonitrile containing an inorganic base such as potassium or cesium carbonate or an organic base such N-ethyl diisopropylamine at an elevated temperature of 40-150° C. P may be hydrogen or a suitable protecting group for an alcohol known to those skilled in the art. This could for example be tert-butyl dimethyl silyl or tetrahydropyranyl. The methods for the protection and deprotection of alcohols are described in the textbook *Protective Groups in Organic Synthesis*, T. W. Greene and p. G. M. Wuts, Wiley Interscience, (1991) ISBN 0571623016

Intermediates of formula III were prepared from 2-cyclohexanone as described by Samoshin et al. (*Tet. Lett.* 1994, 35, 7413-7414). Alternatively an appropriately substituted 2-halo-anisole may be metallated with an alkaline metal such as magnesium (Gilman, *Rec. Trav. Chim. Pays-Bas* 1935, 588) or lithium (Hader et al, *J. Organomet. Chem.* 1989, 364, 1-16) and reacted with bis aryl bissulfides. Alternatively 2-halo-anisoles in the case of the halogen being iodide may be coupled using palladium/phosphine catalysis with a thiophenol as described in the general method of Schopfer (*Tetrahdron* 2001, 57, 3069-3073 to give intermediates, after demethylation of the anisole, of formula III.

Intermediates of formula IV are typically commercially available or their syntheses are well described in the literature.

Compounds of formula V where X is O may be prepared by reacting intermediates of formula III with ethylene carbonate to give the O-hydroxyethyl derivative which can then be converted to compounds of formula V. Where L is Cl this could be using carbon tetrachloride and triphenylphosphine in dichloromethane. In the case of tosylate and mesylate this could by the use of tosyl chloride or methane sulfonyl chloride respectively in a solvent such as dichloromethane or tetrahydrofuran. These methods are standard to those skilled in the art. Compounds of formula V where X is carbon may be prepared by the alkylation of suitably substituted 2-iodo-benzylhalides with diethyl malonate in the general procedure described by L. F. Fieser, E. Berliner, *J. Am. Chem. Soc.* 1952, 74, 536 to give 2-iodo-phenylpropionic acids. In the case of X is sulfur, coupling with an appropriate thiophenol using copper catalysis according to the method of Bartl et al, *Collection Czechoslovak Chem. Commun,* 1981, 46, 141 affords the 2-(arylsulfanyl)phenyl propionic acid which can be reduced using standard methods such as borane-tetrahydrofuran complex or lithium aluminium hydride to 2-(arylsulfanyl)phenyl propanol. Activation of the alcohol to nucleophilic displacement can be performed as described above.

Compounds of formula VI may be prepared by the reaction of intermediates of formula II with intermediates of formula XII. The substituents $R^1$-$R^{10}$ are as defined above, X is oxygen, sulphur or $CR^{11}R^{12}$, wherein $R^{11}$ and $R^{12}$ are as defined above, and Z is an iodide. The reaction is typically performed in a suitable solvent such as tetrahydrofuran or diethyl ether containing a coupling agent such as triphenyl phosphine and diethylazodicarboxylate or 1,1'-(Azodicarbonyl)dipiperidine at room temperature.

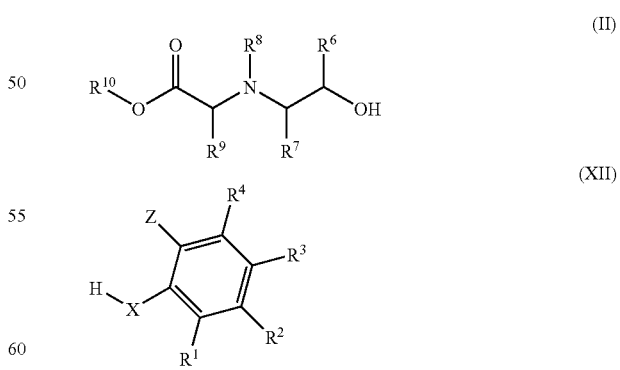

Intermediates of formula XII where Z is an iodide are commercially available or can be easily obtained by demethylation of the corresponding 2-iodo-anisole using for example boron tribromide in toluene or similar methods well known to those skilled in the art. Alternatively treatment of the corresponding anisole with tert-butyl lithium and quenching with iodine as described by Iwao (*J. Org. Chem.* 1990, 55, 3622-3627) and subsequent demethylation will also provide intermediates of formula XII. A third approach is the conversion of the appropriate 2-methoxy aniline derivative to the iodide in a Sandineyer reaction as described by Still (*J. Org. Chem.* 1987, 52, 748-753), followed by demethylation to give intermediates of formula XII. These methods are all well described in the literature.

Examples of formula I may also be prepared by modifications of formula I where $R^1$-$R^4$ can be a bromide or iodide and $R^{10}$ is as defined above but not hydrogen. In this approach the intermediates as described may be reacted with for example with a aryl or heteroaryl boronic acid or ester using Suzuki conditions to afford the appropriately substituted aryl or heteroaryl derivative. Alternatively reaction with an amine using palladium catalysis allows access to examples where the bromide or iodide is replaced with the amine in examples of formula I.

EXAMPLES

General Methods

Analytical LC-MS data were obtained on a PE Sciex API 150EX instrument equipped with IonSpray source and Shimadzu LC-8A/SLC-10A LC system. Column: 30×4.6 mm Waters Symmmetry C18 column with 3.5 μm particle size; Solventsystem: A=water/trifluoroacetic acid (100:0.05) and B=water/acetonitrile/trifluoroacetic acid (5:95:0.03); Method: Linear gradient elution with 90% A to 100% B in 4 min and with a flow rate of 2 mL/min. Purity was determined by integration of the UV (254 nm) and ELSD trace. The retention times (RT) are expressed in minutes.

Preparative LC-MS-purification was performed on the same instrument. Column: 50×20 mm YMC ODS-A with 5 μm particle size; Method: Linear gradient elution with 80% A to 100% B in 7 min and with a flow rate of 22.7 mL/min. Fraction collection was performed by split-flow MS detection.

$^1$H NMR spectra were recorded at 500.13 MHz on a Bruker Avance DRX500 instrument or at 250.13 MHz on a Bruker AC 250 instrument. Deuterated methylenechloride (99.8% D), chloroform (99.8% D) or dimethyl sulfoxide (99.8% D) were used as solvents. TMS was used as internal reference standard. Chemical shift values are expressed in ppm-values. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet and b=broad singlet.

For ion-exchange chromatography, the following material was used: SCX-columns (1 g) from Varian Mega Bond Elut®, Chrompack cat. No. 220776. Prior to use, the SCX-columns were pre-conditioned with 10% solution of acetic acid in methanol (3 mL). For de-complexation by irradiation, a ultra-violet light source (300 W) from Philipps was used.

Polymerbound PPh$_3$ (0.93 mmol/g, 100-200 mesh) was purchased from Senn Chemicals.

Preparation of Intermediates of Formula XI

1-Cyclohexylamino-propan-2-ol

Cyclohexanone (0.98 g, 10 mmol) and 1-amino-propan-2-ol (0.75 g, 10 mmol) were mixed and MeOH (20 mL), acetic acid (12 mg, 0.5 mmol), cyanoborohydride resin (7 g, 14 mmol, 2 mmol/g, prepared as described by A. R. Sande et al, *Tetrahedron Letters* 1984, 3501) were added. The reaction mixture was heated under reflux for 16 h. The resin was filtered off and the filtrate was evaporated in vacuo. The crude product was used without further purification.

2-(tert-Butyl-dimethyl-silanyloxy)-propylamine tert-Butyl-chloro-dimethyl-silane (2.6 g 17 mmol) was dissolved in DCM (20 mL). 1-Amino-propan-2-ol (1.2 g, 16 mmol), triethylamine (2.2 mL, 16 mmol) and a catalytic amount of DMAP were added. The reaction mixture was stirred for 16 h. Water (10 mL) was added and the phases were separated. The aqueous phase was extracted with EtOAc (2×100 mL). The combined organic phases were dried over magnesium sulfate, filtered and the filtrate was evaporated in vacuo. The product was isolated as an oil. Yield: 2.4 g, 80%.

The following intermediates were prepared in an analogous fashion:
2-(tert-Butyl-dimethyl-silanyloxy)-1-methyl-ethylamine
1-(tert-Butyl-dimethyl-silanyloxymethyl)-propylamine
1-(tert-Butyl-dimethyl-silanyloxymethyl)-2-methyl-propylamine
1-(S)-2-(tert-Butyl-dimethyl-silanyloxy)-)-methyl-ethylamine
1-(R)-2-(tert-Butyl-dimethyl-silanyloxy)-methyl-ethylamine Preparation of Intermediates of Formula II (2-Hydroxymethyl-piperidin-1-yl)-acetic acid tert-butyl ester Bromo-acetic acid tert-butyl ester (0.39 g, 2 mmol) was dissolved in DMF (1 mL). A solution of piperidin-2-yl-methanol (0.25 g, 2.2 mmol) in DMF (1 mL) and diisopropylethylamine (0.38 mL, 2.2 mmol) was added. The reaction mixture was stirred at 50° C. for 16 h. The solvent was removed in vacuo. EtOAc (20 mL) and water (7 mL) was added. The two phases were separated. The aqueous phase was extracted twice with EtOAc (20 mL). The combined EtOAc phases were dried over magnesium sulfate, filtered and the filtrate was evaporated in vacuo. The product was isolated as an oil. Yield: 0.37 g, 80%.

The following intermediates were prepared in an analogous fashion:
[(2-Hydroxy-ethyl)-methyl-amino]-acetic acid tert-butyl ester
[Ethyl-(2-hydroxy-ethyl)-amino]-acetic acid tert-butyl ester
[(2-Hydroxy-ethyl)-isopropyl-amino]-acetic acid tert-butyl ester
(4-Hydroxy-piperidin-1-yl)-acetic acid tert-butyl ester
(3-Hydroxy-pyrrolidin-1-yl)-acetic acid tert-butyl ester
(R)-(3-Hydroxy-pyrrolidin-1-yl)-acetic acid tert-butyl ester
2-(3-Hydroxy-pyrrolidin-1-yl)-propionic acid tert-butyl ester
(S)-(3-Hydroxy-pyrrolidin-1-yl)-acetic acid tert-butyl ester
(S)-2-(3-Hydroxy-pyrrolidin-1-yl)-propionic acid tert-butyl ester
[Cyclohexyl-(2-hydroxy-propyl)-amino]-acetic acid tert-butyl ester

[2-(tert-Butyl-dimethyl-silanyloxy)-propylamino]-acetic acid tert-butyl ester 2-(tert-Butyl-dimethyl-silanyloxy)-propylamine (6.0 g, 31.6 mmol) was dissolved in DMF (60 mL). Diisopropylethylamine (5.5 mL, 31.6 mmol) and bromo-acetic acid tert-butyl ester (3.6 g, 18.6 mmol) was added. The reaction mixture was stirred at 50° C. for 16 h. The mixture was evaporated onto silica gel and and purified by column chromatography using a gradient, starting eluting with ethyl acetate/heptane 20:80 up to ethyl acetate/heptane 80:20. The product was isolated as an oil. Yield: 4.0 g, 71%.

The following intermediates were prepared in an analogous fashion:
[2-(tert-Butyl-dimethyl-silanyloxy)-1-methyl-ethylamino]-acetic acid tert-butyl ester
[1-(tert-Butyl-dimethyl-silanyloxymethyl)-propylamino]-acetic acid tert-butyl ester
[1-(tert-Butyl-dimethyl-silanyloxymethyl)-2-methyl-propylamino]-acetic acid tert-butyl ester
(S)-[2-(tert-Butyl-dimethyl-silanyloxy)-1-methyl-ethylamino]-acetic acid
(R)-[2-(tert-Butyl-dimethyl-silanyloxy)-1-methyl-ethylamino]-acetic acid tert-butyl ester

[Ethyl-(2-hydroxy-propyl)-amino]-acetic acid tert-butyl ester

[2-(tert-Butyl-dimethyl-silanyloxy)-propylamino]-acetic acid tert-butyl ester (1.2 g, 4 mmol) and diisopropylethylamine (9.7 mL, 56 mmol) was dissolved in DMF (20 mL). Iodo-ethane (2.6 mL, 32 mmol) was added. The reaction was stirred at 50° C. for 16 h. The solvent was removed in vacuo. The crude product was dissolved in EtOAc (100 mL) and the solution was washed with water (20 mL). The organic phase was dried over magnesium sulfate, filtered and the filtrate was evaporated in vacuo.

The residue was dissolved in acetonitrile (30 mL) and Et$_3$N 3HF (1.3 mL, 8 mmol) was added. The reaction was stirred for 16 h. The solvent was removed in vacuo. The crude product was dissolved in EtOAc (100 mL) and washed with saturated sodium bicarbonate solution (25 mL) and saturated sodium chloride solution (25 mL). The organic phase was dried over magnesium sulfate and the solution was slowly filtered through 5 g of silica gel. The filtrate was evaporated in vacuo. Yield: 0.17 g, 20%.

The following intermediates were prepared in an analogous fashion:
[Ethyl-(2-hydroxy-1-methyl-ethyl)-amino]-acetic acid tert-butyl ester
[Ethyl-(1-hydroxymethyl-propyl)-amino]-acetic acidtert-butyl ester
[Ethyl-(1-hydroxymethyl-2-methyl-propyl)-amino]-acetic acid tert-butyl ester
(S)-[Ethyl-(2-hydroxy-1-methyl-ethyl)-amino]-acetic acid tert-butyl ester
(R)-[Ethyl-(2-hydroxy-1-methyl-ethyl)-amino]-acetic acid tert-butyl ester Preparation of Intermediates of Formula II

[(1-Hydroxymethyl-2-methyl-propyl)-methyl-amino]-acetic acid tert-butyl ester

{[1-(tert-Butyl-dimethyl-silanyloxymethyl)-2-methyl-propyl]-amino}-acetic acid tert-butyl ester (1.9 g, 6.1 mmol) and diisopropylethylamine (4.2 mL, 24 mmol) were dissolved in DMF (15 mL). A solution of MeI (0.45 mL, 7.3 mmol) in DMF (100 mL) was slowly added over 15 min. The reaction was stirred for 2½ h. The solvent was removed in vacuo. The residue product was dissolved in EtOAc (100 mL) and the solution was washed with water (20 mL). The organic phase was dried over magnesium sulfate, filtered and the filtrate was evaporated in vacuo. The residue was dissolved in acetonitrile (45 mL) and Et$_3$N 3HF (2 mL, 12.3 mmol) was added. The reaction was stirred for 16 h. The solvent was removed in vacuo. The crude product was dissolved in EtOAc (100 mL) and washed with saturated sodium bicarbonate solution (25 mL) and saturated sodium chloride solution (25 mL). The organic phase was dried over magnesium sulfate and the solution was slowly filtered through 5 g of silica gel. The filtrate was evaporated in vacuo. Yield: 1.1 g, 78%.

The following intermediates were prepared in an analogous fashion:
[(2-Hydroxy-1-methyl-ethyl)-methyl-amino]-acetic acid tert-butyl ester
[(1-Hydroxymethyl-propyl)-methyl-amino]-acetic acid tert-butyl ester
(S)-[(2-Hydroxy-1-methyl-ethyl)-methyl-amino]-acetic acid tert-butyl ester
(R)-[(2-Hydroxy-1-methyl-ethyl)-methyl-amino]-acetic acid tert-butyl ester
[(2-Hydroxy-propyl)-methyl-amino]-acetic acid tert-butyl ester Preparation of Intermediates of Formula II using Intermediates of Formula VIII and Intermediates of Formula IX (S)-(2-Hydroxy-ethyl)-pyrrolidine-2-carboxylic acid tert-butyl ester L-Pyrrolidine-2-carboxylic acid tert-butyl ester (0.41 g, 2.4 mmol) was dissolved in DMF (2 mL) containing diisopropylethylamine (1.25 mL, 7.2 mmol). A solution of 2-bromo-ethanol (0.34 mL, 4.8 mmol) in DMF (1 mL) was added. The reaction mixture was stirred at 70° C. for 16 h. The solvent was removed in vacuo. EtOAc (20 mL) and saturated sodium bicarbonate solution (10 mL) was added. The aqueous phase was extracted twice with EtOAc (20 mL). The combined EtOAc phases were dried over magnesium sulfate, filtered and the filtrate was evaporated in vacuo. The product was isolated as an oil. Yield: 0.37 g, 72%.

The following intermediate was prepared in an analogous fashion:
(S)-1-(2-Hydroxy-propyl)-pyrrolidine-2-carboxylic acid tert-butyl ester Preparation of Intermediates of Formula III 2-(4-Chloro-phenoxy)-phenol The compound was synthesised as described by G. W. Yeager, D. N. Schissel, *Synthesis* 1995, 28-30.

The following intermediates were prepared in an analogous fashion:
2-(3,4-Difluoro-phenoxy)-phenol
2-(3-Fluoro-phenoxy)-phenol
2-(3-Chloro-phenoxy)-phenol
2-(4-Methoxy-phenoxy)-phenol 3-Chloro-2-iodoanisole A solution of 3-chloroanisole (1.753 g, 12.3 mmol) in THF (60 mL) was cooled to −95° C. A solution of sec-BuLi in cyclohexane (1.3M, 9.5 mL, 12.4 mmol) was added dropwise keeping the internal temperature below −90° C. After 1 h a solution of 12 (3.15 g, 12.4 mmol) in THF (5 mL) was added dropwise. The mixture was allowed to reach room temperature overnight. Diethylether (100 mL) was added. The organic layer was washed with 1M aqueous Na$_2$SO$_3$, H$_2$O, brine and dried over Na$_2$SO$_4$. The crude product was adsorbed onto silica gel. After purification by flash chromatography using silica gel, eluting with heptanes/EtOAc, 98:2, the product was obtained as colorless crystals Yield: 2.19 g, 66%.

4-Bromo-2-iodo-anisole

4-Bromo-anisole (4.417 g, 23.6 mmol) was dissolved in acetonitrile (200 mL) and placed under an argon atmosphere in the absence of light. Iodobenzene diacetate (9.18 g, 28.5 mmol) was added followed by iodine (3.6 g, 14.2 mmol). The mixture was stirred for 16 hours at ambient temperature. The mixture was then poured into 1M $Na_2S_2O_3$ (200 mL) and stirred until the solution was colourless. The solution was then extracted with diethyl ether (3×100 mL). The combined organic extracts were then washed with brine, dried with $Na_2SO_4$, filtered and evaporated to dryness. The crude product was filtered through a silica gel plug eluting with heptane/ethyl acetate (3:1) (200 mL). The filtrate was concentrated and the residue was distilled using a Kugelrohr apparatus collecting the compound at 75° C., 0.01 mbar.

Yield 4.092 g, 55%.

5-Bromo-2-iodo-anisole

4-Bromo-2-methoxy-aniline (20 g, 99 mmol) was dissolved in water (695 mL) and concentrated sulphuric acid (113 mL). The solution was cooled to 0° C. and sodium nitrite (7.5 g, 109 mmol) dissolved in water (32 mL) was added and stirred for 1 hour at 5-10° C. Potassium iodide (21.4 g, 129 mmol) dissolved in water (100 mL) was added slowly whilst the mixture was vigorously stirred. After addition, the mixture was allowed to warm to room temperature. Ethyl acetate was added and the phases were separated. The aqueous phase was extracted with ethyl acetetate (3×). The combined organic phases were then washed with 1M NaOH, 1M $Na_2S_2O_3$, 1M HCl, 1M saturated $NaHCO_3$ and brine. The separated organic phase was dried ($MgSO_4$), filtered and concentrated in vacuo. The product was purified by flash chromatography using silica gel and eluting with heptane/ethyl acetate 1:1. The product was identified from relevant fractions which were combined and concentrated in vacuo.

Yield: 24.12 g, 78%

3-Chloro-2-(3-fluoro-phenylsulfanyl)-phenol

A dry round bottomed flask was charged with NaO$^t$Bu (398 mg, 4.14 mmol), CuI (62 mg, 0.33 mmol), neocuproin (66 mg, 0.30 mmol), 3-fluoro-thiophenol (394 mg, 3.07 mmol) and 3-chloro-2-iodoanisole (698 mg, 2.60 mmol). The flask was evacuated and backfilled with Ar three times. Dry toluene (10 mL) was added and the mixture stirred at 105° C. overnight. The mixture was diluted with toluene (40 mL) and filtered through a pad of silica gel and evaporated to dryness to give a quantitative yield of crude 1-Chloro-2-(3-fluoro-phenylsulfanyl)-3-methoxy-benzene. The material was dissolved in toluene (20 mL) and cooled to 0° C. Neat BBr$_3$ (0.38 mL, 4.02 mmol) was added dropwise and the mixture was allowed to reach room temperature overnight. The mixture was quenched by the addition of $H_2O$/ice (80 mL) and diethyl ether (100 mL). The organic layer was washed with brine. After drying over $Na_2SO_4$ the crude product was adsorbed onto silica gel. After flash chromatography using silica gel, eluting with heptanes/EtOAc, 96:4 the title compound was obtained as a yellow oil Yield: 642 mg, 97% over two steps.

4-Chloro-1-(3-fluoro-phenylsulfanyl)-2-methoxy-benzene

A dry round bottomed flask was charged with KO$^t$Bu (1.903 g, 17.0 mmol), 5-chloro-2-iodoanisole (4.054 g, 15.1 mmol), Pd$_2$dba$_3$ (144 mg, 0.16 mmol), DPEPhos (176 mg, 0.33 mmol) and 3-fluoro-thiophenol (1.903 g, 17.0 mmol). The flask was evacuated and backfilled with Ar three times. Dry toluene (80 mL) was added and the mixture stirred at 95° C. for 2 h. The mixture was filtered through a pad of silica gel followed by adsorption onto silica gel. After purification by flash chromatography using silica gel, eluting with heptanes/EtOAc, 97:3, the title compound was obtained as a yellow oil (3.41 g, 85%).

and the following compounds was prepared in an analogous fashion:
4-Bromo-2-(3-fluoro-phenylsulfanyl)-1-methoxy-benzene
5-Bromo-2-(3-fluoro-phenylsulfanyl)-1-methoxy-benzene
4-Phenyl-2-(3-fluoro-phenylsulfanyl)-1-methoxy-benzene
4-Cyano-2-(3-fluoro-phenylsulfanyl)-1-methoxy-benzene

5-Chloro-2-(3-fluoro-phenylsulfanyl)-phenol

A solution of 4-chloro-1-(3-fluoro-phenylsulfanyl)-2-methoxybenzene (3.12 g, 11.6 mmol) in dry toluene (60 mL) was cooled to 0° C. Neat BBr$_3$ (1.50 mL, 15.9 mmol) was added dropwise and the mixture was allowed to reach room temperature overnight. The mixture was quenched by the addition of $H_2O$/ice (50 mL) and diethyl ether (50 mL). The aqueous layer was extracted with diethylether (2×50 mL). The combined organic layers were washed with brine, dried over $Na_2SO_4$ and adsorbed onto silica gel. After flash chromatography using silica gel, eluting with heptanes/EtOAc, 95:5, the title compound was obtained as a light yellow oil (2.26 g, 77%).

The following phenols were prepared in an analogous fashion:
2-Chloro-6-(3-fluoro-phenylsulfanyl)-phenol
4-Chloro-2-(3-fluoro-phenylsulfanyl)-phenol
4-Bromo-2-(3-fluoro-phenylsulfanyl)-phenol
5-Bromo-2-(3-fluoro-phenylsulfanyl)-phenol
4-Phenyl-2-(3-fluoro-phenylsulfanyl)-phenol
4-Cyano-2-(3-fluoro-phenylsulfanyl)-phenol Preparation of Intermediates V for Example 2

2-(2-Iodo-benzyl)-malonic acid diethyl ester

Sodium (0.19 g, 8.2 mmol) was dissolved in absolute ethanol (12 mL). The solution was cooled on an ice bath. Malonic acid diethyl ester (1.3 g, 8.1 mmol) was added. A solution of 1-chloromethyl-2-iodo-benzene (2.0 g, 7.9 mmol) in absolute ethanol (6 mL) cooled on an ice bath was added to the malonic acid diethyl ester solution. The solution, which deposited sodium chloride, was let stand at 0° C. for 4 h and at room temperature overnight. The solution was neutralised with HCl (4N). The solvent was removed in vacuo and the residue was dissolved in dichloromethane (25 mL). Water (15 mL) was added and the phases were separated. The aqueous phase was reextracted with dichloromethane (10 mL). The combined organic fractions were dried ($Na_2SO_4$), filtered and evaporated. Yield: 2.86 g, 92%.

3-(2-Iodo-phenyl)-propionic acid

Concentrated HCl (2.3 mL) and water (0.3 mL) was added to 2-(2-iodo-benzyl)-malonic acid diethyl ester (1.4 g, 3.6 mmol) and the mixture was refluxed overnight. Starting material could still be seen on TLC. More concentrated HCl (2 mL) was added and the mixture was refluxed overnight. Water (20 mL) and ether (50 mL) was added to the mixture. The two phases were separated. The organic phase was extracted with an ammonium hydroxide solution (5N, 30 mL). The basic water phase was added slowly to ice-cold conc. HCl. The white precipitate was filtered and washed with ice-cold water and the solvent was removed in vacuo. Yield: 0.32 g, 32%.

3-[2-(3-Fluoro-phenylsulfanyl)-phenyl]-propionic acid 3-(2-Iodo-phenyl)-propionic acid (0.3 g, 1.1 mmol) was dissolved in water (2.8 mL). 3-Fluoro-benzenethiol (0.13 g, 0.99 mmol), KOH (0.15 g, 2.6 mmol) and Cu (13 mg, 0.2 mmol) was added. The mixture was refluxed overnight. The hot solution was filtered and the filtrate was made acidic with concentrated HCl. The mixture was extracted with dichloromethane (2×25 mL). The combined organic phases were washed with water (15 mL), dried ($MgSO_4$), filtered and evaporated. Yield: 0.26 g, 96%.

3-[2-(3-Fluoro-phenylsulfanyl)-phenyl]-propan-1-ol $LiAlH_4$ (46 mg, 1.22 mmol) was suspended in ether (1.7 mL). A solution of 3-[2-(3-fluoro-phenylsulfanyl)-phenyl]-propionic acid (2.6 g, 0.94 mmol) in ether (1.7 mL) was added slowly. The reaction was stirred for 4 h at room temperature. Excess $LiAlH_4$ was hydrolysed with water. The mixture was made acidic using HCl (4N). Ether (20 mL) was added. The two phases were separated and the organic phase was washed with NaOH (2N) and then with water. The organic phase was dried ($MgSO_4$), filtered and evaporated. Yield: 0.14 g, 55%.

1-(3-Iodo-propyl)-2-(3-fluro-phenylsulfanyl)-benzene

Polymerbound $PPh_3$ (0.49 g, 0.46 mmol) was suspended in dichloromethane (4.5 mL). Imidazole (0.03 g, 0.46 mmol) and 12 (0.12 g, 0.46 mmol) was added and the mixture was stirred for 5 minutes. A solution of 3-[2-(3-Fluoro-phenylsulfanyl)-phenyl]-propan-1-ol (0.096 g, 0.37 mmol) in dichloromethane (0.5 mL) was added and the mixture was stirred for 4 h at room temperature. The resin was filtered off and washed with dichloromethane (2 mL). The filtrate was washed with $Na_2S_2O_3$ (2×2 mL) and water (2 mL). The organic phase was dried ($MgSO_4$), filtered and evaporated. Yield: 0.096 g, 71%.

2-[3-(3-Fluoro-phenylsulfanyl)-biphenyl-4-yloxy]-ethanol 3-(3-Fluoro-phenylsulfanyl)-biphenyl-4-ol (2.65 g, 8.94 mmol) and potassium carbonate (2.113 g, 15.3 mmol) was dissolved in DMF (30 mL). Ethylene carbonate (1.601 g, 18.2 mmol) was added and the reaction was heated at 100° C. for 150 minutes. The solution was allowed to cool before the solution was carefully poured into 2M HCl (50 mL). The product was extracted with diethyl ether (50 mL). The separated organic phase was washed with water (4×50 mL), 4% aq. $MgSO_4$, brine and then the separated organic phase was dried ($MgSO_4$). The title product was isolated after concentration in vacuo. Yield: 2.96 g, 97%

Preparation of Intermediate of Formula VI for Example 4

(S)-1-[2-(5-Chloro-2-iodo-phenoxy)-ethyl]-pyrrolidine-2-carboxylic acid tert-butyl ester 5-Chloro-2-iodophenol (801 mg, 3.15 mmol) and $PPh_3$ (1.15 g, 4.41 mmol) were dissolved in THF (25 mL). DIAD (0.91 mL, 4.62 mmol). was added dropwise and the solution was stirred for 20 min. A solution of 1-(2-hydroxy-ethyl)-pyrrolidine-2-(S)-carboxylic acid tert butyl ester (816 mg, 3.79 mmol) in THF (4 mL) was added via canulation. The mixture was stirred for 40 min at 0° C. then for 1.5 h at room temperature and finally for 3 h at 50° C. The mixture was diluted with heptanes (100 mL), washed with water (4×25 mL), dried over $Na_2SO_4$ and evaporated onto silica gel. After flash chromatography using silica gel, eluting with heptanes/EtOAc, 9:1, the title compound was obtained as a colorless oil (1.023 g, 72%).

And the following intermediate was prepared in an analogous fashion:
(S)-1-[2-(3-Iodo-biphenyl-4-yloxy)-ethyl]-pyrrolidine-2-carboxylic acid tert-butyl ester Preparation of Intermediates of Formula XII

3-Iodo-biphenyl-4-ol

Biphenyl-4-ol((5.26 g, 30.9 mmol), sodium iodide (4.635 g, 30.9 mmol), sodium hydroxide (1.276 g, 31.9 mmol) was dissolved in methanol (85 mL) and cooled to 0° C. To the solution was added 12% (w/v) sodium hypochlorite (20 mL) dropwise maintaining the temperature below 4° C. The solution was stirred at this temperature for 1 hour and then 2M sodium thiosulfite (50 mL) wad added and the pH of the solution was adjusted to >pH 7 with 1M HCl. The mixture was filtered and the filtrate was washed with water. The solid was dried in a vacuum oven and then the title product was obtained as crystals after recrystallisation from heptane. Yield 7.08 g, 77%.

Preparation of Intermediates of Formula I used in preparation of examples 5-5f, 6 and 6b

(S)-1-{2-[4-Bromo-2-(3-fluoro-phenylsulfanyl)-phenoxy]-ethyl}-pyrrolidine-2-carboxylic acid tert-butyl ester 4-Bromo-2-(3-fluoro-phenylsulfanyl)-phenol (2.898 g, 9.69 mmol) and triphenylphosphine (3.558 g, 13.6 mmol) was dissolved in tetrahydrofuran (70 mL) and cooled to 0° C. under an inert atmosphere. To the solution was added DEAD (2.81 mL, 14.27 mmol)dropwise. After 25 minutes was added 1-(2-hydroxy-ethyl)-pyrrolidine-2-(S)-carboxylic acid tert-butyl ester (2.504 g, 1.163 mmol) in THF (15 mL) via cannulation. The mixture was stirred at room temperature for 16 hours. Heptane (350 mL) and THF (100 mL) was added. The organic phase was then washed with water (4×50 mL) and then brine, dried ($Na_2SO_4$), filtered and the filtrate concentrated in the presence of silica gel. The crude products absorbed onto silica gel and eluted with a gradient of heptane-heptane ethyl acetate (85:15). The product was isolated after concentration of relevant fractions.

Yield: 3.342 g, 69%

And the following intermediate was prepared in an analogous fashion:
(S)-1-{2-[5-Bromo-2-(3-fluoro-phenylsulfanyl)-phenoxy]-ethyl}-pyrrolidine-2-carboxylic acid tert-butyl ester Preparation of Compounds of the Invention

Example 1

1aa (S)-1-{2-[2-(4-Fluoro-phenylsulfanyl)-phenoxy]-ethyl}-pyrrolidine-2-carboxylic acid A solution of L-1-(2-Hydroxy-ethyl)-pyrrolidine-2-carboxylic acid tert-butyl ester (0.068 mmol) in THF (0.5 mL) was added to polymerbound $PPh_3$ (75 mg, 0.07 mmol). A solution of 2-(3-Fluoro-phenylsulfanyl)-phenol (0.04 mmol) in THF (0.5 mL) and a solution of DEAD (0.068 mmol) in THF (0.5 mL) added. The reaction was stirred at room temperature for 16 h. The resin was filtered off and washed with methanol (2×1 mL) and THF (1 mL). The solvents were removed by evaporation in vacuo. HCl in acetic acid (1 M, 1.5 mL) was added and the mixture was stirred for 16 h. The solvent was removed in vacuo. The crude product was purified by preparative LC-MS.

LC/MS (m/z) 362.2 (MH$^+$); RT=1.97; purity (UV, ELSD): 93%, 100%; yield: 7.5 mg.

The following compounds were prepared in an analogous fashion:

1ab (S)-1-(2-[2-(4-tert-Butyl-phenylsulfanyl)-phenoxy]-ethyl)-pyrrolidine-2-carboxylic acid from (S)-1-(2-Hydroxy-ethyl)-pyrrolidine-2-carboxylic acid tert-butyl ester LC/MS (m/z) 400.1 (MH$^+$); RT=2.45; purity (UV, ELSD): 96%, 100%; yield: 6.2 mg.

1ac (S)-1-{2-[2-(4-Trifluoromethyl-phenylsulfanyl)-phenoxy]-ethyl)-pyrrolidine-2-carboxylic acid from (S)-1-(2-Hydroxy-ethyl}-pyrrolidine-2-carboxylic acid tert-butyl ester LC/MS (m/z) 412.0 (MH$^+$); RT=2.21; purity (UV, ELSD): 99%, 100%; yield: 5.5 mg.

1ad (S)-1-{2-[2-(3-Fluoro-phenylsulfanyl)-phenoxy]-ethyl}-pyrrolidine-2-carboxylic acid from (S)-1-(2-Hydroxy-ethyl)-pyrrolidine-2-carboxylic acid tert-butyl ester LC/MS (m/z) 362.2 (MH$^+$); RT=1.98; purity (UV, ELSD): 95%, 100%; yield: 4.8 mg.

1ae (S)-{2-[2-(4-Chloro-phenylsulfanyl)-phenoxy]-ethyl}-pyrrolidine-2-carboxylic acid from (S)-1-(2-Hydroxy-ethyl)-pyrrolidine-2-carboxylic acid tert-butyl ester LC/MS (m/z) 378.1 (MH$^+$); RT=2.12; purity (UV, ELSD): 93%, 100%; yield: 5.1 mg.

1af (S)-1-{2-[2-(3-Chloro-phenylsulfanyl)-phenoxy]-ethyl}-pyrrolidine-2-carboxylic acid from (S)-1-(2-Hydroxy-ethyl)-pyrrolidine-2-carboxylic acid tert-butyl ester LC/MS (m/z) 378.1; RT=2.10; purity (UV, ELSD): 98%, 100%; yield: 3.3 mg.

1ag (S)-1-{2-[2-(3,4-Dichloro-phenylsulfanyl)-phenoxy]-ethyl}-pyrrolidine-2-carboxylic acid from (S)-1-(2-Hydroxy-ethyl)-pyrrolidine-2-carboxylic acid tert-butyl ester LC/MS (m/z) 412.0; RT=2.28; purity (UV, ELSD): 99%, 100%; yield: 5.2 mg.

1ah (S)-1-{2-[2-(3-Chloro-4-fluoro-phenylsulfanyl)-phenoxy]-ethyl}-pyrrolidine-2-carboxylic acid from (S)-1-(2-Hydroxy-ethyl)-pyrrolidine-2-carboxylic acid tert-butyl ester LC/MS (m/z) 396.1; RT=2.15; purity (UV, ELSD): 98%, 100%; yield: 4.5 mg.

1ai (S)-1-{2-[2-(3-Chloro-phenoxy)-phenoxy]-ethyl}-pyrrolidine-2-carboxylic acid from (S)-1-(2-Hydroxy-ethyl)-pyrrolidine-2-carboxylic acid tert-butyl ester LC/MS (m/z) 362.1; RT=2.02; purity (UV, ELSD): 96%, 100%; yield: 12.1 mg.

1aj (S)-1-{2-[2-(4-Chloro-phenoxy)-phenoxy]-ethyl}-pyrrolidine-2-carboxylic acid from (S)-1-(2-Hydroxy-ethyl)-pyrrolidine-2-carboxylic acid tert-butyl ester LC/MS (m/z) 362.2(MH$^+$); RT=2.12; purity (UV, ELSD): 95%, 99%; yield: 12.7 mg.

1ak (S)-1-{2-[2-(4-Methoxy-phenoxy)-phenoxy]-ethyl}-pyrrolidine-2-carboxylic acid from (S)-1-(2-Hydroxy-ethyl)-pyrrolidine-2-carboxylic acid tert-butyl ester LC/MS (m/z) 358.0(MH$^+$); RT=1.83; purity (UV, ELSD): 100%, 99%; yield: 13.8 mg.

1al (S)-1-{2-[2-(3,4-Difluoro-phenoxy)-phenoxy]-ethyl}-pyrrolidine-2-carboxylic acid from (S)-1-(2-Hydroxy-ethyl)-pyrrolidine-2-carboxylic acid tert-butyl ester LC/MS (m/z) 364.2 (MH$^+$); RT=1.95; purity (UV, ELSD): 100%, 99%; yield: 13.8 mg.

1am 1-{2(R/S)-[2-(4-Chloro-phenoxy)-phenoxy]-propyl}-pyrrolidine-2(S)-carboxylic acid from (S)-1-(2(R/S)-Hydroxy-propyl)-pyrrolidine-2-carboxylic acid tert-butyl ester LC/MS (m/z) 376.1 (MH$^+$); RT=2.12; purity (UV, ELSD): 99%, 99%; yield: 4.1 mg.

1an 1-{2(R/S)-[2-(3,4-Difluoro-phenoxy)-phenoxy]-propyl}-pyrrolidine-2(S)-carboxylic acid from L-1-(2(R/S)-Hydroxy-propyl)-pyrrolidine-2-carboxylic acid tert-butyl ester LC/MS (m/z) 378.1 (MH$^+$); RT=2.07; purity (UV, ELSD): 96%, 99%; yield: 3.4 mg.

1ao (S)-1-{2-[2-(3-Fluoro-phenoxy)-phenoxy]-ethyl}-pyrrolidine-2-carboxylic acid from (S)-1-(2-Hydroxy-ethyl)-pyrrolidine-2-carboxylic acid tert-butyl ester LC/MS (m/z) 346.2(MH$^+$); RT=1.99; purity (ELSD): 95%; yield: 3.44 mg.

1ap 1-{2(R/S)-[2-(3-Fluoro-phenoxy)-phenoxy]-propyl}-pyrrolidine-2(S)-carboxylic acid from L-1-(2(R/S)-Hydroxy-propyl)-pyrrolidine-2(S)-carboxylic acid tert-butyl ester LC/MS (m/z) 360.3(MH$^+$); RT=2.02; purity (UV, ELSD): 70%, 98%; yield: 7.2 mg.

1aq 1-{2(R/S)-[2-(3-Fluoro-phenylsulfanyl)-phenoxy]-propyl}-pyrrolidine-2(S)-carboxylic acid from 1-(2(R/S)-Hydroxy-propyl)-pyrrolidine-2(S)-carboxylic acid tert-butyl ester LC/MS (m/z) 376.1 (MH$^+$); RT=2.10; purity (UV, ELSD): 99%, 98%; yield: 4.3 mg.

1ar 1-{2(R/S)-[2-(3-Chloro-phenylsulfanyl)-phenoxy]-propyl}-pyrrolidine-2(S)-carboxylic acid from 1-(2(R/S)-Hydroxy-propyl)-pyrrolidine-2(S)-carboxylic acid tert-butyl ester LC/MS (m/z) 392.2 (MH$^+$); RT=2.23; purity (UV, ELSD): 94%, 88.9%; yield: 2.1 mg.

1as ({2-[2-(4-tert-Butyl-phenylsulfanyl)-phenoxy]-ethyl}-N-ethyl-amino)-acetic acid from [Ethyl-(2-hydroxy-ethyl)-amino]-acetic acid tert-butyl ester LC/MS (m/z) 388.2 (MH$^+$); RT=2.53; purity (UV, ELSD): 94%, 95%; yield: 5.6 mg 1at 2-{3-[2-(4-tert-Butyl-phenylsulfanyl)-phenoxy]-pyrrolidin-2-yl}-propionic acid from 2-(3-Hydroxy-pyrrolidin-1-yl)-propionic acid tert-butyl ester LC/MS (m/z) 400.0 (MH$^+$); RT=2.40; purity (UV, ELSD): 94%, 100%; yield: 4.2 mg 1au ({2-[2-(3-Chloro-phenylsulfanyl)-phenoxy]-ethyl}-N-methyl-amino)-acetic acid from [(2-Hydroxy-ethyl)-methyl-amino]-acetic acid tert-butyl ester LC/MS (m/z) 351.9 (MH$^+$); RT=2.02; purity (UV, ELSD): 98%, 100%; yield: 9.9 mg 1av ({2-[2-(3-Chloro-4-fluoro-phenylsulfanyl)-phenoxy]-ethyl}-N-methyl-amino)-acetic acid from [(2-Hydroxy-ethyl)-methyl-amino]-acetic acid tert-butyl ester LC/S (m/z) 370.0 (MH$^+$); RT=2.07; purity (UV, ELSD): 93%, 100%; yield: 6.7 mg 1aw {2-[2-(4-tert-Butyl-phenylsulfanyl)-phenoxymethyl]-piperidin-1-yl}-acetic acid from (2-Hydroxymethyl-piperidin-1-yl)-acetic acid tert-butyl ester LC/MS (m/z) 414.4 (MH$^+$); RT 2.52=; purity (UV, ELSD): 100%, 100%; yield: 2.6 mg 1ax ({2-[2-(3-Fluoro-phenylsulfanyl)-phenoxy]-ethyl}-N-methyl-amino)-acetic acid from [(2-Hydroxy-ethyl)-methyl-amino]-acetic acid tert-butyl ester LC/MS (m/z) 336.2 (MH$^+$); RT=1.96; purity (UV, ELSD): 96%, 95%; yield: 1.8 mg 1ay {4-[2-(4-tert-Butyl-phenylsulfanyl)-phenoxy]-piperidin-1-yl}-acetic acid from (4-Hydroxy-piperidin-1-yl)-acetic acid tert-butyl ester LC/MS (m/z) 400.0 (MH$^+$); RT=2.48; purity (UV, ELSD): 89%, 100%; yield: 5.5 mg 1az (N-2-propyl-{2-[2-(4-trifluoromethyl-phenylsulfanyl)-phenoxy]-ethyl}-amino)-acetic acid from [(2-Hydroxy-ethyl)-isopropyl-amino]-acetic acid tert-butyl ester LC/MS (m/z) 414.2 (MH$^+$); RT=2.26; purity (UV, ELSD): 95%, 100%; yield: 2.4 mg 1ba ({2-[2-(3,4-Dichloro-phenylsulfanyl)-phenoxy]-ethyl}-N-ethyl-amino)-acetic acid from [Ethyl-(2-hydroxy-ethyl)-amino]-acetic acid tert-butyl ester LC/MS (m/z) 400.1 (MH$^+$); RT=2.27; purity (UV, ELSD): 99%, 100%; yield: 8.3 mg 1bb (N-Ethyl-{2-[2-(4-methylsulfanyl-phenylsulfanyl)-phenoxy]-ethyl}-amino)-acetic acid from [Ethyl-(2-hydroxy-ethyl)-amino]-acetic acid tert-butyl ester LC/MS (m/z) 378.3 (MH$^+$); RT=2.13; purity (UV, ELSD): 99%, 100%; yield: 8.5 mg 1bc 2-{3-[2-(3,4-Dichloro-phenylsulfanyl)-phenoxy]-pyrrolidin-1-yl}-propionic acid from 2-(3-Hydroxy-pyrrolidin-1-yl)-propionic acid tert-butyl ester LC/MS (m/z) 412.0 (MH$^+$); RT=2.25; purity (UV, ELSD): 100%, 100%; yield: 7.5 mg 1bd (S)-{3-[2-(4-tert-Butyl-phenylsulfanyl)-phenoxy]-pyrrolidin-1-yl}-acetic acid from (R)-(3-Hydroxy-pyrrolidin-1-yl)-acetic acid tert-butyl ester LC/MS (m/z) 386.0 (MH$^+$); RT=2.42; purity (UV, ELSD): 90%, 95%; yield: 2.2 mg 1be ({2-[2-(3-Chloro-4-fluoro-phenylsulfanyl)-phenoxy]-ethyl}-N-ethyl-amino)-acetic acid from [Ethyl-(2-hydroxy-ethyl)-amino]-acetic acid tert-butyl ester LC/MS (m/z) 384.2 (MH$^+$); RT=2.15; purity (UV, ELSD): 97%, 100%; yield: 8.2 mg 1bf (N-2-propyl-{2-[2-(4-methylsulfanyl-phenylsulfanyl)-phenoxy]-ethyl}-amino)-acetic acid from [(2-Hydroxy-ethyl)-isopropyl-amino]-acetic acid tert-butyl ester LC/MS (m/z) 392.2 (MH⁺); RT=2.17; purity (UV, ELSD): 97%, 99%; yield: 9.9 mg 1bg {3-[2-(4-tert-Butyl-phenylsulfanyl)-phenoxy]-pyrrolidin-1-yl}-acetic acid from (3-Hydroxy-pyrrolidin-1-yl)-acetic acid tert-butyl ester LC/MS (m/z) 386.0 (MH⁺); RT=2.38; purity (UV, ELSD): 96%, 100%; yield: 3.1 mg 1bh ({2-[2-(3-Chloro-phenylsulfanyl)-phenoxy]-ethyl}-N-ethyl-amino)-acetic acid from [Ethyl-(2-hydroxy-ethyl)-amino]-acetic acid tert-butyl ester LC/MS (m/z) 366.2); RT=2.10; purity (UV, ELSD): 100%, 100%; yield: 11.5 mg 1bi ({2-[2-(4-Chloro-phenylsulfanyl)-phenoxy]-ethyl-}N-methyl-amino)-acetic acid from [(2-Hydroxy-ethyl)-methyl-amino]-acetic acid tert-butyl ester LC/MS (m/z) 352.2 (MH⁺); RT=2.12; purity (UV, ELSD): 78%, 97%; yield: 2.2 mg 1bj {4-[2-(3,4-Dichloro-phenylsulfanyl)-phenoxy]-piperidin-1-yl}-acetic acid from (4-Hydroxy-piperidin-1-yl)-acetic acid tert-butyl ester LC/MS (m/z) 412.1 (MH⁺); RT=2.32; purity (UV, ELSD): 99%, 100%; yield: 5.9 mg 1bk 2-{3-[2-(4-Trifluoromethyl-phenylsulfanyl)-phenoxy]-pyrrolidin-1-yl}-propionic acid from 2-(3-Hydroxy-pyrrolidin-1-yl)-propionic acid tert-butyl ester LC/MS (m/z) 412.1 (MH⁺); RT=2.17; purity (UV, ELSD): 99%, 100%; yield: 6.1 mg 1bl ({2-[2-(4-tert-Butyl-phenylsulfanyl)-phenoxy]-ethyl}-N-2-propyl-amino)-acetic acid from [(2-Hydroxy-ethyl)-isopropyl-amino]-acetic acid tert-butyl ester LC/MS (m/z) 402.2 (MH⁺); RT=2.57; purity (UV, ELSD): 90%, 98%; yield: 8.3 mg 1bm ({2-[2-(4-tert-Butyl-phenylsulfanyl)-phenoxy]-ethyl}-N-methyl-amino)-acetic acid from [(2-Hydroxy-ethyl)-methyl-amino]-acetic acid tert-butyl ester LC/MS (m/z) 373.8 (MH⁺); RT=2.34; purity (UV, ELSD): 91%, 100%; yield: 8.9 mg 1bn {2-[2-(4-Methylsulfanyl-phenylsulfanyl)-phenoxymethyl]-piperidin-1-yl}-acetic acid from (2-Hydroxymethyl-piperidin-1-yl)-acetic acid tert-butyl ester LC/MS (m/z) 404.2 (MH⁺); RT=2.21; purity (UV, ELSD): 98%, 100%; yield: 2.6 mg 1bo ({2-[2-(3,4-Dichloro-phenylsulfanyl)-phenoxy]-ethyl}-N-methyl-amino)-acetic acid from [(2-Hydroxy-ethyl)-methyl-amino]-acetic acid tert-butyl ester LC/MS (m/z) 385.8 (MH⁺); RT=2.19; purity (UV, ELSD): 95%, 100%; yield: 8.1 mg 1bp (N-Methyl-{2-[2-(4-trifluoromethyl-phenylsulfanyl)-phenoxy]-ethyl}-amino)-acetic acid from [(2-Hydroxy-ethyl)-methyl-amino]-acetic acid tert-butyl ester LC/MS (m/z) 386.0 (MH⁺); RT=2.13; purity (UV, ELSD): 95%, 100%; yield: 5.3 mg 1bq -2-{3(R)-[2-(4-tert-Butyl-phenylsulfanyl)-phenoxy]-pyrrolidin-1-yl}-propionic acid from (S)-2-(3-Hydroxy-pyrrolidin-1-yl)-propionic acid tert-butyl ester LC/MS (m/z) 400.1 (MH⁺); RT=2.44; purity (UV, ELSD): 97%, 100%; yield: 9.2 mg 1br 2-{3(R)-[2-(3,4-Dichloro-phenylsulfanyl)-phenoxy]-pyrrolidin-1-yl}-propionic acid from (S)-2-(3-Hydroxy-pyrrolidin-1-yl)-propionic acid tert-butyl ester LC/MS (m/z) 412.1 (MH⁺); RT=2.26; purity (UV, ELSD): 100%, 98%; yield: 9.4 mg 1bs 2-[3(R)-(2-(4-methylphenyl)-sulfanyl-phenoxy)-pyrrolidin-1yl]-propionic acid from (S)-2-(3-Hydroxy-pyrrolidin-1-yl)-propionic acid tert-butyl ester LC/MS (m/z) 358.2 (MH⁺); RT=2.06; purity (UV, ELSD): 98%, 98%; yield: 8.1 mg 1bt {3(2)-[2-(4-tert-Butyl-phenylsulfanyl)-phenoxy]-pyrrolidin-1-yl}-acetic acid from (S)-(3-Hydroxy-pyrrolidin-1-yl)-acetic acid tert-butyl ester LC/MS (m/z) 386.2 (MH⁺); RT=2.38; purity (UV, ELSD): 94%, 99%; yield: 3.0 mg 1bu 2-{3(R)-[2-(4-Trifluoromethyl-phenylsulfanyl)-phenoxy]-pyrrolidin-1-yl}-propionic acid from (S)-2-(3-Hydroxy-pyrrolidin-1-yl)-propionic acid tert-butyl ester LC/MS (m/z) 412.2 (MH⁺); RT=2.20; purity (UV, ELSD): 98%, 100%; yield: 9.5 mg 1bv 2-{3(R)-[2-(4-Chloro-phenylsulfanyl)-phenoxy]-pyrrolidin-1-yl}-propionic acid from (S)-2-(3-Hydroxy-pyrrolidin-1-yl)-propionic acid tert-butyl ester LC/MS (m/z) 378.1 (MH$^+$); RT=2.13; purity (UV, ELSD): 91%, 100%; yield: 6.3 mg 1bw ({1-[2-(3-Chloro-phenylsulfanyl)-phenoxymethyl]-propyl}-N-ethyl-amino)-acetic acid from [Ethyl-(1-hydroxymethyl-propyl)-amino]-acetic acid tert-butyl ester LC/MS (m/z) 394.2 (MH$^+$); RT=2.29; purity (UV, ELSD): 97%, 99%; yield: 4.8 mg 1bx ({1-[2-(3,4-Dichloro-phenylsulfanyl)-phenoxy]-butan-2-yl}-N-ethyl-amino)-acetic acid from [Ethyl-(1-hydroxymethyl-propyl)-amino]-acetic acid tert-butyl ester LC/MS (m/z) 428.1 (MH$^+$); RT=2.46; purity (UV, ELSD): 94%, 100%; yield: 4.6 mg 1by ({1-[2-(3,4-Dichloro-phenylsulfanyl)-phenoxy]-butan-3-methyl-2-yl}-N-ethylamino)-acetic acid from [Ethyl-(1-hydroxymethyl-2-methyl-propyl)-amino]-acetic acid tert-butyl ester LC/MS (m/z) 442.2 (MH$^+$); RT=2.56; purity (UV, ELSD): 96%, 100%; yield: 1.0 mg 1bz ({1-[2-(3-Chloro-4-fluoro-phenylsulfanyl)-phenoxy]-butan-2-yl}-N-ethyl-amino)-acetic acid from [Ethyl-(1-hydroxymethyl-propyl)-amino]-acetic acid tert-butyl ester LC/MS (m/z) 412.1 (MH$^+$); RT=2.32; purity (UV, ELSD): 99%, 100%; yield: 4.7 mg 1ca ({1-[1-(3-Chloro-phenylsulfanyl)-phenoxy]-propan-2-yl}-N-ethyl-amino)-acetic acid from [Ethyl-(2-hydroxy-1-methyl-ethyl)-amino]-acetic acid tert-butyl ester LC/MS (m/z) 380.1 (MH$^+$); RT=2.18; purity (UV, ELSD): 99%, 100%; yield: 4.8 mg 1cb ({1-[2-(3-Chloro-4-fluoro-phenylsulfanyl)-phenoxy]-butan-3-methyl-2-yl)}-N-ethyl-amino)-acetic acid from [Ethyl-(1-hydroxymethyl-2-methyl-propyl)-amino]-acetic acid tert-butyl ester LC/MS (m/z) 426.2 (MH$^+$); RT=2.42; purity (UV, ELSD): 90%, 100%; yield: 0.9 mg 1cc ({1-[2-(3-Chloro-4-fluoro-phenylsulfanyl)-phenoxy]propan-2-yl}-N-ethyl-amino)-acetic acid from [Ethyl-(2-hydroxy-1-methyl-ethyl)-amino]-acetic acid tert-butyl ester LC/MS (m/z) 398.2 (MH$^+$); RT=2.12; purity (UV, ELSD): 96%, 100%; yield: 3.1 mg 1cd (S)-({1-[2-(3-Chloro-phenylsulfanyl)-phenoxy]-propan-2-yl}-N-methyl-amino)-acetic acid from (S)-[(2-Hydroxy-1-methyl-ethyl)-methyl-amino]-acetic acid tert-butyl ester LC/MS (m/z) 366.2 (MH$^+$); RT=2.08; purity (UV, ELSD): 98%, 97%; yield: 4.4 mg 1ce (S)-({1-[2-(3-Chloro-phenylsulfanyl)-phenoxy]-propan-2-yl}-N-ethyl-amino)-acetic acid from (S)-[Ethyl-(2-hydroxy-1-methyl-ethyl)-amino]-acetic acid tert-butyl ester LC/MS (m/z) 380.2 (MH$^+$); RT=2.18; purity (UV, ELSD): 72%, 100%; yield: 1.3 mg 1cf ({1-[2-(3,4-Dichloro-phenylsulfanyl)-phenoxy]-propan-2-yl}-N-ethyl-amino)-acetic acid from [Ethyl-(2-hydroxy-1-methyl-ethyl)-amino]-acetic acid tert-butyl ester LC/MS (m/z) 416.2 (MH$^+$); RT 2.34; purity (UV, ELSD): 100%, 100%; yield: 4.9 mg 1cg ({1-[2-(4-Chloro-phenylsulfanyl)-phenoxy]-propan-2-yl}-N-ethyl-amino)-acetic acid from [Ethyl-(2-hydroxy-1-methyl-ethyl)-amino]-acetic acid tert-butyl ester LC/MS (m/z) 380.3 (MH$^+$); RT=2.19; purity (UV, ELSD): 94%, 100%; yield: 3.9 mg 1ch ({1-[2-(3-Chloro-phenylsulfanyl)-phenoxymethyl]-propyl}-N-methyl-amino)-acetic acid from [(1-Hydroxymethyl-propyl)-methyl-amino]-acetic acid tert-butyl ester LC/MS (m/z) 380.2 (MH$^+$); RT=2.21; purity (UV, ELSD): 98%, 100%; yield: 3.6 mg 1ci ({1-[2-(4-Chloro-phenylsulfanyl)-phenoxymethyl]-propyl}-N-ethyl-amino)-acetic acid from [Ethyl-(1-hydroxymethyl-propyl)-amino]-acetic acid tert-butyl ester LC/MS (m/z) 394.3 (MH$^+$); RT=2.33; purity (UV, ELSD): 96%, 100%; yield: 4.5 mg 1cj (N-Ethyl-{1-[2-(3-fluoro-phenylsulfanyl)-phenoxymethyl]-propyl}-amino)-acetic acid from [Ethyl-(1-hydroxymethyl-propyl)-amino]-acetic acid tert-butyl ester LC/MS (m/z) 378.3 (MH$^+$); RT=2.16; purity (UV, ELSD): 99%, 100%; yield: 5.7 mg 1ck (R)-({2-[2-(3,4-Dichloro-phenylsulfanyl)-phenoxy]-1-methyl-ethyl}-N-ethyl-amino)-acetic acid from (R)-[Ethyl-(2-hydroxy-1-methyl-ethyl)-amino]-acetic acid tert-butyl ester LC/MS (m/z) 416.0 (MH$^+$); RT=2.35; purity (UV, ELSD): 92%, 100%; yield: 1.5 mg 1cl (S)-(2-{1-[2-(4-Chloro-phenoxy)-phenoxy]-propan-2-yl}-N-methyl-amino)-acetic acid from (S)-[(2-Hydroxy-1-methyl-ethyl)-methyl-amino]-acetic acid tert-butyl ester LC/MS (m/z) 350.1 (MH+); RT=2.00; purity (UV, ELSD): 96%, 97%; yield: 2.6 mg 1cm (R)-(2-{1-[2-(3-Chloro-phenylsulfanyl)-phenoxy]-propan-2-}-N-methyl-amino)-acetic acid from (R)-[(2-Hydroxy-1-methyl-ethyl)-methyl-amino]-acetic acid tert-butyl ester LC/MS (m/z) 366.1 (MH+); RT=2.10; purity (UV, ELSD): 98%, 98%; yield: 6.1 mg 1cn ({2-[2-(3-Fluoro-phenylsulfanyl)-phenoxy]-propyl}-N-methyl-amino)-acetic acid from [(2-Hydroxy-propyl)-methyl-amino]-acetic acid tert-butyl ester LC/MS (m/z) 350.1 (MH+); RT=1.97; purity (UV, ELSD): 81%, 99%; yield: 2.2 mg 1co ({2-[2-(3-Chloro-phenylsulfanyl)-phenoxy]-propan-1yl}-N-ethyl-amino)-acetic acid from [Ethyl-(2-hydroxy-propyl)-amino]-acetic acid tert-butyl ester LC/MS (m/z) 380.3 (MH+); RT=2.19; purity (UV, ELSD): 97%, 98%; yield: 2.9 mg 1cp ({1-[2-(3-Chloro-phenylsulfanyl)-phenoxy]-3-methyl-butan-2-yl}-N-methylamino)-acetic acid from [(1-Hydroxymethyl-2-methyl-propyl)-methyl-amino]-acetic acid tert-butyl ester LC/MS (m/z) 394.2 (MH+); RT=2.31; purity (UV, ELSD): 93%, 100%; yield: 2.3 mg 1cq ({3-methyl-1-[2-(4-trifluoromethyl-phenylsulfanyl)-phenoxy]-butan-2-yl}-N-ethylamino)-acetic acid from [Ethyl-(1-hydroxymethyl-2-methyl-propyl)-amino]-acetic acid tert-butyl ester LC/MS (m/z) 442.3 (MH+); RT=2.46; purity (UV, ELSD): 98%, 100%; yield: 1.7 mg 1cr ({1-[2-(3-Chloro-4-fluoro-phenylsulfanyl)-phenoxy]-butan-2-yl}-N-methylamino)-acetic acid from [(1-Hydroxymethyl-propyl)-methyl-amino]-acetic acid tert-butyl ester LC/MS (m/z) 398.1 (MH+); RT=2.24; purity (UV, ELSD): 96%, 98%; yield: 8.1 mg 1cs (S)-({1-[2-(3-Chloro-4-fluoro-phenylsulfanyl)-phenoxy]-propan-2-yl}N-methyl-amino)-acetic acid from (S)-[(2-Hydroxy-1-methyl-ethyl)-methyl-amino]-acetic acid tert-butyl ester LC/MS (m/z) 384.1 (MH+); RT=2.16; purity (UV, ELSD): 97%, 100%; yield: 3.7 mg 1ct (S)-({1-[2-(3-Fluoro-phenylsulfanyl)-phenoxy]-propan-2yl}-N-methyl-amino)-acetic acid from (S)-[(2-Hydroxy-1-methyl-ethyl)-methyl-amino]-acetic acid tert-butyl ester LC/MS (m/z) 350.1 (MH+); RT=1.97; purity (UV, ELSD): 91%, 97%; yield: 5.5 mg 1cu ({-[2-(4-tert-Butyl-phenylsulfanyl)-phenoxy]-3-methyl-butan-2-yl}-N-ethylamino)-acetic acid from [Ethyl-(1-hydroxymethyl-2-methyl-propyl)-amino]-acetic acid tert-butyl ester LC/MS (m/z) 430.2 (MH+); RT=2.73; purity (UV, ELSD): 83%, 100%; yield: 1.0 mg 1cv (S)-({1-[2-(3,4-Dichloro-phenylsulfanyl)-phenoxy]-propan-2-yl}-N-methyl-amino)-acetic acid from (S)-[(2-Hydroxy-1-methyl-ethyl)-methyl-amino]-acetic acid tert-butyl ester LC/MS (m/z) 400.0 (MH+); RT=2.27; purity (UV, ELSD): 100%, 98%; yield: 3.5 mg 1cw ({1-[2-(3-Chloro-4-fluoro-phenylsulfanyl)-phenoxy]-3-methyl-butan-2-yl}-N-methyl-amino)-acetic acid from [(1-Hydroxymethyl-2-methyl-propyl)-methyl-amino]-acetic acid tert-butyl ester LC/MS (m/z) 412.0 (MH+); RT=2.35; purity (UV, ELSD): 87%, 97%; yield: 3.0 mg 1cx ({1-[2-(4-tert-Butyl-phenylsulfanyl)-phenoxy]-propan-2-yl}-N-ethyl-amino)-acetic acid from [Ethyl-(2-hydroxy-1-methyl-ethyl)-amino]-acetic acid tert-butyl ester LC/MS (m/z) 402.2 (MH+); RT=2.53; purity (UV, ELSD): 90%, 99%; yield: 3.4 mg 1cy ({2-[2-(3-Chloro-4-fluoro-phenylsulfanyl)-phenoxy]-propan-1-yl}-N-ethylamino)-acetic acid from [Ethyl-(2-hydroxy-propyl)-amino]-acetic acid tert-butyl ester LC/MS (m/z) 398.1 (MH+); RT=2.24; purity (UV, ELSD): 86%, 96%; yield: 2.3 mg 1cz ({2-[2-(4-methoxy-phenylsulfanyl)-phenoxy]-propan-1-yl}-N-Cyclohexylamino)-acetic acid from [Cyclohexyl-(2-hydroxy-propyl)-amino]-acetic acid tert-butyl ester LC/MS (m/z) 430.3 (MH+); RT=2.32; purity (UV, ELSD): 83%, 80%; yield: 1.5 mg 1da {[2-(2-(4-methylsulfanyl-phenoxy)-propan-1-yl-]-N-cyclohexyl-amino}-acetic acid from [Cyclohexyl-(2-hydroxy-propyl)-amino]-acetic acid tert-butyl ester LC/MS (m/z) 414.4 (MH+); RT=2.50; purity (UV, ELSD): 79%, 100%; yield: 1.1 mg 1db ({2-[2-(3-Chloro-phenylsulfanyl)-phenoxy]-propan-1-yl}-N-cyclohexyl-amino)-acetic acid from [Cyclohexyl-(2-hydroxy-propyl)-amino]-acetic acid tert-butyl ester LC/MS (m/z) 434.9 (MH$^+$); RT=2.50; purity (UV, ELSD): 98%, 84%; yield: 2.1 mg Example 2

(S)-1-{3-[2-(3-Fluoro-phenylsulfanyl)-phenyl]-propanyl}-pyrrolidine-2-carboxylic acid hydrochloride 1-(3-Iodo-propyl)-2-(3-fluro-phenylsulfanyl)-benzene (48 mg, 0.13 mmol) was dissolved in DMF (0.4 mL). S-Pyrrolidine-2-carboxylic acid tert-butyl ester (22 mg, 0.13 mmol) and diisopropylethylamine (25 μL, 0.14 mmol) were added. The mixture was stirred at 50° C. for 6 h and then at room temperature overnight. The solvent was removed in vacuo. The residue was dissolved in HCl/AcOH (3.1 mL) and stirred overnight. The solvent was removed in vacuo. The crude product was purified by preparative LC-MS.

Yield: 16.2 mg, 34%

LC/MS (m/z) 360.3+); RT=2.18; purity (UV, ELSD): 89%, 100%

2b (S)-2-({2-[3-(3-Fluoro-phenylsulfanyl)-biphenyl-4-yloxy]-ethyl}-methyl-amino)-propionic acid hydrochloride 2-[3-(3-Fluoro-phenylsulfanyl)-biphenyl-4-yloxy]-ethanol (0.493 mg, 1.45 mmol) was dissolved in dichloromethane, cooled to −78° C. and placed under an inert atmosphere. To the solution was added N-ethyldiisopropylamine (0.63 mL, 3.62 mmol) and then triflic anhydride (0.32 mL, 1.90 mmol), dropwise. The solution was allowed to stir for 40 minutes and then warmed to room temperature. L-N-methylalanine tertbutyl ester (435 mg, 2.22 mmol) was added and the mixture was stirred for 16 hours. Silica gel was added to the mixture and the solvent was removed in vacuo. The products were absorbed onto silica gel and then purified by flash chromatography eluting with heptane/ethyl acetate (90:10). The intermediate butyl ester was isolated after evaporation of relevant fractions. Yield 403 mg, 58% This was then dissolved in 1M HCl/AcOH (5 mL) and stirred at room temperature for 16 hours. The solvent was then removed in vacuo to give the title compound as a white solid.

Yield: 235 mg, 60%

$^1$H NMR (DMSO, 500 MHz) 1.33 (d, 3H), 2.33 (s, 1H), 2.64 (s, 3H), 3.35 (m, 2H), 4.1 (m, 1H), 4.4 (m, 2H), 6.9 (m, 3H), 7.1-7.2 (m, 2H), 7.2 (m, 2H), 7.37 (m, 3H), 7.55 (m, 1H)

and the following compound was prepared in an analogous fashion 2c ({2-[3-(3-Fluoro-phenylsulfanyl)-biphenyl-4-yloxy]-ethyl}-methyl-amino)-acetic acid from 2-[3-(3-Fluoro-phenylsulfanyl)-biphenyl-4-yloxy]-ethanol Yield: 282 mg, 54% over two steps $^1$H NMR (CHCl$_3$, 500 MHz) 2.45 (s, 1H), 2.7 (s, 21), 3.45 (m, 2H), 3.98 (s, 2H), 4.42 (m, 2H), 6.92 (m, 3H), 7.15 (m, 2H), 7.24 (m, 2H), 7.4 (dd, 3H), 7.55 (dd, 1H)

LC/MS (m/z) 412.5 (MH$^+$); RT=2.53; purity (UV, ELSD): 95.1%, 99.6%

Example 3

3a (S)-1-{2-[4-Chloro-2-(3-fluoro-phenylsulfanyl)-phenoxy]-ethyl}-pyrrolidine-2-carboxylic acid hydrochloride A solution of 4-Chloro-2-(3-fluoro-phenylsulfanyl)-phenol (290 mg, 1.14 mmol), PPh$_3$ (398 mg, 1.52 mmol) in dry THF (6 mL) was cooled to 0° C. DEAD (0.25 mL, 1.59 mmol) was added dropwise and the solution was stirred for 20 min. A solution of 1-(2-hydroxy-ethyl)-pyrrolidine-2-(S)-carboxylic acid tert butyl ester (370 mg, 1.72 mmol) in TBF (4 mL) was added via canulation. The mixture was stirred for 40 min at 0° C. then for 1.5 h at room temperature and finally for 3 h at 50° C. The mixture was diluted with heptanes (100 mL), washed with water (4×25 mL), dried over Na$_2$SO$_4$ and evaporated onto silica gel. After flash chromatography using silica gel, eluting with heptanes/EtOAc, 9:1, the intermediate tert butyl ester was obtained as a colorless oil (393 mg, 76%). To a solution of the ester (380 mg, 0.84 mmol) in glacial HOAc (10 mL) was added HCl in HOAc (1M, 10 mL). The mixture was stirred at room temperature overnight. The solution was evaporated to dryness to give the title compound as a colourless foam Yield: 367 mg, 100%.

$^1$H NMR (CDCl$_3$, 500 MHz) 2.01 (br, 2H), 2.19 (br, 1H), 2.44 (br, 1H), 3.21 (br, 1H), 3.57 (br, 1H), 3.94 (br, 2H), 4.42 (br, 2H), 4.67 (br, 1H), 6.92-7.00 (m, 3H), 7.03-7.06 (m, 1H), 7.11 (br, 1H), 7.21-7.25 (m, 1H), 7.28-7.33 (m, 1H).

LC-MS (m/z) 396.0 (MH$^+$); RT=2.31; purity (UV, ELSD): 97.1%, 97.9%.

The following compounds were prepared in an analogous fashion:

3b (S)-1-{2-[3-Chloro-2-(3-fluoro-phenylsulfanyl)-phenoxy]-ethyl}pyrrolidine-2-carboxylic acid hydrochloride from of 3-Chloro-2-(3-fluoro-phenylsulfanyl)-phenol Yield 452 mg $^1$H NMR (CDCl$_3$, 500 GHz) 1.86-1.94 (br, 2H), 2.18 (br, 1H), 2.34 (br, 1H), 3.11 (br, 1H), 3.50 (br, 1H), 3.74 (br, 1H), 3.89 (br, 1H), 4.39 (br, 2H), 4.65 (br, 1H), 6.67 (d, 1H), 6.76-6.79 (m, 2H), 6.98-7.00 (m, 1H), 7.18-7.21 (m, 2H), 7.33-7.36 (m, 1H).

LC-MS (m/z) 396.1 (MH$^+$); RT=2.21; purity (UV, ELSD): 95.1%, 98.7%.;

3c (S)-1-{2-[5-Chloro-2-(3-fluoro-phenylsulfanyl)-phenoxy]-ethyl}pyrrolidine-2-carboxylic acid hydrochloride from of 5-Chloro-2-(3-fluoro-phenylsulfanyl)-phenol Yield: 539 mg $^1$H NMR (CDCl$_3$, 500 MHz) 2.01 (br, 2H), 2.21 (br, 1H), 2.41 (br, 1H), 3.19 (br, 1H), 3.57 (br, 1H), 3.90 (br, 1H), 4.41 (br, 2H), 4.65 (br, 2H), 6.92-6.96 (m, 3H), 7.01-7.06 (m, 2H), 7.14-7.29 (m, 2H).

LC-MS (m/z) 396.1 (MH$^+$); RT=2.28; purity (UV, ELSD): 93.7%, 99.9% yield 539 mg

3d (S)-1-{2-[4-Cyano-2-(3-fluoro-phenylsulfanyl)-phenoxy]-ethyl}-pyrrolidine-2-carboxylic acid from 4-cyano-2-(3-fluoro-phenylsulfanyl)-phenol Yield: 257 mg, 100%

$^1$H NMR (CDCl$_3$, 500 MHz) 1.82 (m, 1H), 1.97 (m, 2H), 2.35 (m, 1H), 3.13 (dd, 1H), 3.3 (m, 2H), 3.68 (d, 1H), 4.3 (t, 1H), 4.5 (m, 2H), 7.2 (m, 2H), 7.3 (d, 1H), 7.45 (m, 1H), 7.55 (s, 1H), 7.88 (d, 1H)

LC-MS (m/z) 387 (MH$^+$); RT=1.98; purity (UV/ELSD) 98.4%, 91.7%

Example 4

4a (S)-1-[2-(5-Chloro-2-phenylsulfanyl-phenoxy)-ethyl]pyrrolidine-2-carboxylic acid hydrochloride A dry round bottomed flask was charged with 1-[2-(5-Chloro-2-iodo-phenoxy)-ethyl]-pyrrolidine-2-(S)-carboxylic acid tert-butyl ester (301 mg, 0.666 mmol), toluene (4.5 mL), KO$^t$BU (100 mg, 0.89 mmol), thiophenol (78 mg, 0.708 mmol). The mixture was evacuated and backfilled with argon three times. A separate dry round-bottomed flask was charged with Pd$_2$dba$_3$ (9.6 mg, 0.010 mmol) and DPEPhos (16 mg, 0.030 mmol), evacuated and backfilled with argon three times. Toluene (1.5 mL) was added and the mixture stirred at room temperature for 10 min. 1.0 mL of the catalyst mixture was added to the reaction mixture via syringe, and the reaction mixture was heated to 90° C. for 3 h. The mixture was diluted with heptane (6 mL), filtered and adsorbed onto silica gel. After purification by flash chromatography using silica gel, eluting with heptane/EtOAc, 92:8, the tert-butyl ester was obtained as a yellow oil (209 mg, 72%). To a solution of the tert-butyl ester (200 mg) in glacial HOAc (10 mL) was added HCl in HOAc (1M, 10 mL). The mixture was stirred at room temperature overnight. The solution was evaporated to dryness to give the title compound as a colorless foam. Yield: 136 mg, 54%

$^1$H NMR (500 MHz, CDCl$_3$) 2.05 (br, 2H), 2.27 (br, 1H), 2.45 (br, 1H), 3.24 (br, 1H), 3.58 (br, 1H), 3.95 (br, 2H), 4.43 (br, 2H), 4.66 (br, 1H), 6.85-7.00 (m, 2H), 7.13 (br, 1H), 7.26-7.38 (m, 5H). LC-MS (m/z) 377.9 (MH$^+$); RT=2.20 min; purity (UV, ELSD): 99.9%, 96.4%; yield 136 mg and the following compound was prepared in an analogous fashion

4b (S)-1-{2-[3-(3-Fluoro-phenylsulfanyl)-biphenyl-4-yloxy]-ethyl}-pyrrolidine-2-carboxylic acid hydrochloride from (S)-1-[2-(3-Iodo-biphenyl-4-yloxy)-ethyl]-pyrrolidine-2-carboxylic acid tert-butyl ester and 3-fluoro-thiophenol Yield 63 mg, 13%

$^1$H NMR (500 MHz, CDCl$_3$) 1.82 (m, 1H), 1.92 (m, 1H), 2.15 (m, 1H), 2.3 (m, 1H), 3.02 (m, 1H), 3.46 (br m, 1H), 3.73 (m, 1H), 3.82 (m, 1H), 4.1-4.4 (br m, 2H), 4.65 (m, 1H), 6.7 (dd, 2H), 6.85 (d, 1H), 6.95 (m, 1H), 7.1 (d, 1H), 7.2 (m, 1H), 7.26 (dd, 1H), 7.32 (m, 2H), 7.4 (m, 2H)

LC-MS (m/z) 438.5 (MH$^+$); RT=2.51; purity (UV/ELSD) 94.0%, 99.3%

Example 5

5a (S)-{2-[4'-Methoxy-3-(3-fluoro-phenylsulfanyl)-biphenyl-4-yloxy]-ethyl}-pyrrolidine-2-carboxylic acid hydrochloride 1-{2-[4-Bromo-2-(3-fluoro-phenylsulfanyl)-phenoxy]-ethyl}-pyrrolidine-2(S)-carboxylic acid tert-butyl ester (387 mg, 0.78 mmol), 4-methoxyphenyl boronic acid (202 mg, 1.33 mmol) and K$_2$CO$_3$ (296 mg, 2.14 mmol) was dissolved in dimethoxyethane (6 mL) and water (3 mL) and solution was degassed with nitrogen for 10 minutes. Bis(triphenylphosphine)palladium (II) chloride (29 mg, 0.041 mmol) was added and the mixture was heated at 85° C. for 2 hours. The mixture was then cooled to room temperature and diluted with diethylether. The organic layer was separated and then washed with saturated aqueous sodium bicarbonate (10 mL) and then dried (MgSO$_4$). To the filtrate was added silica gel and the product was absorbed on to the silica gel during evaporation of the solvent in vacuo. The product was then purified by flash chromatography using a gradient of heptane/ethyl acetate 92:8 to heptane/ethyl acetate 85:15 on a Flashmaster silica gel column. Concentration in vacuo of relevant fractions afforded the intermediate butyl ester. Yield. 300 mg, 73%. This was then dissolved in 1M HCl/AcOH (10 mL) and the solution was stirred at room temperature for 16 hours. The solution was then evaporated to dryness and the product dried in a vacuum oven. Yield 299 mg, 104%.

$^1$H NMR (500 MHz, CDCl$_3$) 1.93 (br m, 1H), 2.05 (br m, 1H), 2.35-2.45 (br m, 2H), 3.11 (br m, 1H), 3.5 (br m, 1H), 3.8 (s, 3H), 3.9 (br m, 2H), 4.3 (br m, 1H), 4.45 (br m, 1H), 4.7 (br m, 1H), 6.87 (m, 2H), 6.94 (m, 3H), 7.0 (br m, 1H), 7.2 (br m, 1H), 7.39 (d, 2H), 7.49 (m, 1H), 7.55 (m, 1H)

LC-MS (m/z) 468.5 (MH$^+$); RT=2.51 min; purity (UV, ELSD): 86.9%, 98.4% and the following compounds were prepared in an analogous fashion

5b (S)-{2-[4'-Cyano-3-(3-fluoro-phenylsulfanyl)-biphenyl-4-yloxy]-ethyl}-pyrrolidine-2-carboxylic acid hydrochloride from (S)-1-{2-[4-Bromo-2-(3-fluoro-phenylsulfanyl)-phenoxy]-ethyl}-pyrrolidine-2-carboxylic acid tert-butyl ester Yield: 274 mg $^1$H NMR (500 MHz, DMSO) 1.78 (m, 1H), 1.95 (m, 2H), 2.28 (m, 1H), 3.11 (dd, 1H), 3.5 (m, 2H), 3.7 (d, 1H), 4.38 (m, 1H), 4.5 (m, 2H), 7.09 (m, 3H), 7.33 (d, 1H), 7.4 (m, 2H), 7.7 (s, 1H), 7.7-7.8 (m, 5H)

LC-MS (m/z) 463 (MH$^+$); RT=2.2 (UV, ELSD): 93.7%, 89.5%

5c (S)-1-{2-[4'-Cyano-4-(3-fluoro-phenylsulfanyl)-biphenyl-3-yloxy]-ethyl}-pyrrolidine-2-carboxylic acid hydrochloride from (S)-1-{2-[5-Bromo-2-(3-fluoro-phenylsulfanyl)-phenoxy]-ethyl}-pyrrolidine-2-carboxylic acid tert-butyl ester Yield: 285 mg, 56% over two steps $^1$H NMR (500 MHz, DMSO) 1.8 (m, 1H), 2.0 (m, 2H), 2.4 (m, 1H), 3.2 (m, 1H), 3.6 (m, 2H), 3.72 (m, 1H), 3.75 (d, 1H), 4.4 (t, 1H), 4.5 (m, 2H), 7.12 (m, 3H), 7.3 (d, 1H), 7.42 (m, 2H), 7.5 (s, 1H), 7.95 (s, 4H)

LC-MS (m/z) 463 (MH$^+$); RT=2.2 (UV, ELSD): 90%, 100%

$^1$H NMR (500 MHz, DMSO)

5d (S)-1-{2-[2-(3-Fluoro-phenylsulfanyl)-5-thiophen-3-yl-phenoxy]-ethyl}-pyrrolidine-2-carboxylic acid hydrochloride from 1-{2-[5-Bromo-2-(3-fluoro-phenylsulfanyl)-phenoxy]-ethyl}-pyrrolidine-2-carboxylic acid tert-butyl ester Yield: 330 mg, 62% over two steps $^1$H NMR (500 MHz, DMSO) 1.8 (m, 1H), 1.95 (m, 2H), 2.35 (m, 1H), 3.12 (m, 1H), 3.55 (m, 2H), 3.7 (d, 1H), 4.35 (m, 1H), 4.5 (m, 2H), 6.92 (d, 1H), 7.0 (d, 1H), 7.05 (dd, 1H), 7.35-7.5 (m, 4H), 7.68 (m, 2H), 8.06 (s, 1H)

LC-MS (m/z) 444 (MH$^+$); RT=2.45 (UV, ELSD) 93%, 100%

5e (S)-1-{2-[2-(3-Fluoro-phenylsulfanyl)-4-pyrimidine-5-yl-phenoxy]-ethyl}-pyrrolidine-2-carboxylic acid hydrochloride from 1-{2-[4-Bromo-2-(3-fluoro-phenylsulfanyl)-phenoxy]-ethyl}-pyrrolidine-2-carboxylic acid tert-butyl ester Yield: 251 mg, 57% over two steps $^1$H NMR (500 MHz, DMSO) 1.8 (m, 1H), 1.9-2.0 (m, 2H), 2.4 (m, 1H), 3.1 (m, 1H), 3.5 (m, 2H), 3.7 (m, 1H), 4.4 (m, 1H), 4.5 (d, 2H), 7.05 (m, 3H), 7.35 (m, 2H), 7.8 (s, 1H)

LC-MS (m/z) 439.971 (MH$^+$); RT=1.78 (UV, ELSD) 98%, 99%

5f (S)-1-{2-[3-(3-Fluoro-phenylsulfanyl)-3-methanesulfonyl-biphenyl-4-yloxy]-ethyl}-pyrrolidine-2-carboxylic acid hydrochloride from 1-{2-[4-Bromo-2-(3-fluoro-phenylsulfanyl)-phenoxy]-ethyl}-pyrrolidine-2-carboxylic acid butyl ester Yield 390 mg, 61% over two steps $^1$H NMR (500 MHz, DMSO) 1.8 (m, 1H), 1.9 (m, 2H), 2.4 (m, 1H), 3.2 (d, 1H), 3.25 (s, 3H), 3.6 (m, 2H), 3.72 (d, 1H), 4.35 (t, 1H), 4.4 (m, 1H), 7.05 (m, 3H), 7.38 (m, 2H), 7.73 (dd, 1H), 7.82 (s, 1H), 7.85 (d,1H), 7.96 (d, 1H), 8.12 (s, 1H)

LC-MS (m/z) 515.9410 (MH$^+$); RT=2.05 (UV/ELSD) 94%, 94%

Example 6

6a (S)-1-{2-[2-(3-Fluoro-phenylsulfanyl)-4-morpholin-4-yl-phenoxy]-ethyl}-pyrrolidine-2-carboxylic acid hydrochloride 1-{2-[4-Bromo-2-(3-fluoro-phenylsulfanyl)-phenoxy]-ethyl}-pyrrolidine-2(S)-carboxylic acid tert-butyl ester (497 mg, 1.0 mmol) was dissolved in dry tetrahydrofuran (1 mL). Then palladium(II)dibenzylidne acetone (Pd$_2$dba$_3$) (15 mg, 0.016 mmol, 2-(di-tertbutylphosphino)biphenylphosphine (21 mg, 0.07 mmol) and potassium tert-butoxide (159 mg, 1.42 mmol) were added to the vessel placed under an argon atmosphere. Morpholine (0.11 mL, 1.26 mmol) was added to the mixture which was then stirred overnight. The mixture was then diluted with ethyl acetate (25 mL), filtered and then evaporated to dryness. The residue was taken up in acetic acid (10 mL) and 1M HCl/AcOH (10 mL) was added. The solution was stirred at room temperature for 16 hours before being evaporated to dryness. The crude product was then purified by preparative LC-MS. The purified compound was dissolved in acetic acid (30 mL) and 1M HCL/AcOH was added (10 mL). The solvent was removed in vacuo and after reevaporation from dichloromethane the title compound was isolated as a colourless foam.

Yield:162 mg, 34% over two steps.

$^1$H NMR (500 MHz, DMSO) 1.8 (m,1H), 1.9-2.0 (m, 2H), 2.4 (m, 1H), 3.1 (m,1H), 3.2 (br s, 4H), 3.5 (m, 2H), 3.7 (d, 1H), 3.83 (m, 4H), 4.4 (m, 3H), 6.97 (d, 1H), 7.0 (d,1H), 7.08 (dd, 1H), 7.2 (d, 1H), 7.33 (m, 3H)

LC-MS (m/z) 447.5), RT=1.76 (UV/ELSD)=99.8%, 96.4%

6b (S)-1-{2-[2-(3-Fluoro-phenylsulfanyl)-4-piperidin-1-yl-phenoxy]-ethyl}-pyrrolidine-2-carboxylic acid hydrochloride (S)-1-{2-[4-Bromo-2-(3-fluoro-phenylsulfanyl)-phenoxy]-ethyl}-pyrrolidine-2-carboxylic acid tert-butyl ester (990 mg, 1.99 mmol) was dissolved in toluene (4 mL). To the solution was palladium(II)tris(dibenzylidneacetone) (Pd$_2$dba$_3$), sodium tert-butoxide (270 mg, 2.81 mmol) and 2-(dicyclohexylphosphino)biphenyl (15 mg, 0.043 mmol) under an inert atmosphere. To the mixture was added piperidine (0.24 mL, 2.43 mmol) and the mixture was heated to 80° C. for 16 hours. The mixture was allowed to cool to room temperature. The mixture was then diluted with diethyl ether (35 mL) filtered and evaporated to dryness. The residue was then dissolved in ethyl acetate/diethyl ether, silica gel was added and the solvent removed in vacuo. The product absorbed on to silica gel was then placed on a silica cartridge and then eluted with heptane/(heptane:ethyl acetate:triethylamine) 70/30 to 50/50. The intermediate butyl ester was isolated from relevant fractions (244 mg, 0.487 mmol) and then dissolved in acetic acid (10 mL). To the solution was added 1M HCl/AcOH (10 mL) and the solution was stirred for 16 hours. The title compound was isolated after evaporation to dryness.

Yield: 301 mg, 32% over two steps

LC-MS (m/z) 445.0908 (MH$^+$); RT=1.44 (UV/ELSD)= 88%, 98%

Pharmacological Testing

The compounds of the invention were tested in a well-recognised and reliable test measuring glycine uptake:

[$^3$H]-Glycine Uptake

Cells transfected with the human GlyT-1b were seeded in 96 well plates. Prior to the experiment the cells were washed twice in HBS (10 mM Hepes-tris (pH 7.4), 2.5 mM KCl, 1 mM CaCl$_2$, 2.5 mM MgSO$_4$,) and pre-incubated with test compound for 6 minutes. Afterwards, 10 nM $^3$H-glycine was added to each well and the incubation was continued for 15 minutes. The cells were washed twice in HBS. Scintillation fluid was added and the Plates were counted on a Trilux (Wallac) scintillation counter.

The test results showed, that the prepared compounds of the invention all showed inhibition below 10000 nM as IC$_{50}$ in the above-mentioned assay.

The compounds of the invention were also tested in a well-recognised and reliable microdialysis test.

Method

Male Sprague-Dawley rats, initially weighing 275-350 g, were used. The animals were housed under a 12-hr light/dark cycle under controlled conditions for regular indoor temperature (21±2° C.) and humidity (55±5%) with food and tap water available ad libitum.

Rats were anaesthetized with hypnorm/dormicum (2 ml/kg) and intracerebral guide cannulas (CMA/12) were stereotaxically implanted into the brain positioning the dialysis probe tip in the ventral hippocampus (co-ordinates 5.6 mm posterior to bregma, lateral −5.0 mm, 7.0 mm ventral to dura). The rats were allowed to recover from surgery for at least 2 days. On the day of the experiment, a microdialysis probe (CMA/12, 0.5 mm diameter, 3 mm length) was inserted through the guide cannula. The probes were connected via a dual channel swivel to a microinjection pump. Perfusion of the microdialysis probe with filtered Ringer solution (145 mM NaCl, 3 mM KCl, 1 mM MgCl$_2$, 1.2 mM CaCl$_2$) was begun shortly before insertion of the probe into the brain and continued for the duration of the experiment at a constant flow of 1 μl/min. After 165 min of stabilization, the experiments were initiated. A 20 or 40 min sampling regime was used throughout the experimental period. Time points were corrected for lag time of the perfusate from the microdialysis site to the probe outlet.

After the experiments, the rats were sacrificed by decapitation. The brains were removed, frozen and sectioned (20 μm), and the position of the probes was verified.

Analysis of Glycine in the Dialysates

The concentration of glycine in the dialysates was analyzed by means of HPLC with fluorescence detection after precolumn online derivatisation with o-phatalaldehyde. The system consisted of a Hypersil AA-ODS column (5 μm, 2.1× 200 mm, Agilent) with a Agilent 1100 fluoresence detector (excitation, 266-340 nm; emission, 305-340 nm). Mobile phases consisted of A: 20 mM sodium acetate, 0.018% triethylamine, 0.3% tetrahydrofuran, pH 7.2. B: 20 mM sodium acetate, 40% acetonitrile and 40% methanol, pH 7.2. The oven temperature was set at 40° C. and flow rate was 0.45 ml/min. Data were collected and analysed using ChemStation software (Agilent) after calibration with a range of standard glycine solutions (0.1-10 μM).

Data Presentation

The mean value of 3 consecutive glycine samples immediately preceding compound administration served as the basal level for each experiment and data were converted to percentage of basal (mean basal pre-injection values normalized to 100%).

The invention claimed is:
1. A compound of the formula I

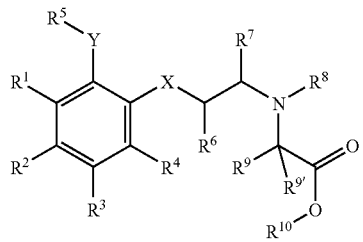

wherein
X is O, S or $CR^{11}R^{12}$, wherein $R^{11}$ and $R^{12}$ are each independently H or $C_{1-6}$ alkyl;
Y is O or S;
$R^1$, $R^2$, $R^3$ and $R^4$ are each independently hydrogen; halogen; cyano; nitro; $C_{1-6}$-alk(en/yn)yl; $C_{1-6}$-alk(en/yn)yloxy; $C_{1-6}$-alk(en/yn)ylsulfanyl; hydroxy; hydroxy-$C_{1-6}$-alk(en/yn)yl; halo-$C_{1-6}$-alk(en/yn)yl; halo-$C_{1-6}$-alk(en/yn)yloxy; $C_{3-8}$-cycloalk(en)yl; $C_{3-8}$-cycloalk(en)yl-$C_{1-6}$-alk(en/yn)yl; acyl; $C_{1-6}$-alk(en/yn)yloxycarbonyl; $C_{1-6}$-alk(en/yn)ylsulfonyl; aryl optionally substituted with a halogen, cyano, nitro, $C_{1-6}$-alk(en/yn)yl, $C_{1-6}$-alk(en/yn)yloxy, $C_{1-6}$-alk(en/yn)ylsulfanyl, hydroxy, hydroxy-$C_{1-6}$-alk(en/yn)yl, halo-$C_{1-6}$-alk(en/yn)yl, halo-$C_{1-6}$-alk(en/yn)yloxy, $C_{3-8}$-cycloalk(en)yl, $C_{3-8}$-cycloalk(en)yl-$C_{1-6}$-alk(en/yn)yl, acyl, $C_{1-6}$-alk(en/yn)yloxycarbonyl or $C_{1-6}$-alk(en/yn)ylsulfonyl; monocyclic heteroaryl optionally substituted with a halogen, cyano, nitro, $C_{1-6}$-alk(en/yn)yl, $C_{1-6}$-alk(en/yn)yloxy, $C_{1-6}$-alk(en/yn)ylsulfanyl, hydroxy, hydroxy-$C_{1-6}$-alk(en/yn)yl, halo-$C_{1-6}$-alk(en/yn)yl, halo-$C_{1-6}$-alk(en/yn)yloxy, $C_{3-8}$-cycloalk(en)yl, $C_{3-8}$-cycloalk(en)yl-$C_{1-6}$-alk(en/yn)yl, acyl, $C_{1-6}$-alk(en/yn)yloxycarbonyl or $C_{1-6}$-alk(en/yn)ylsulfonyl; or $-NR^{13}R^{14}$ wherein $R^{13}$ and $R^{14}$ are each independently hydrogen, $C_{1-6}$-alk(en/yn)yl, $C_{3-8}$-cycloalk(en)yl, $C_{3-8}$-cycloalk(en)yl-$C_{1-6}$ alk(en/yn)yl or aryl, or $R^{13}$ and $R^{14}$ together with the nitrogen atom to which they are attached form a 3-7-membered heterocyclic ring which optionally contains one further heteroatom selected from O, S and N;

$R^5$ is aryl or monocyclic heteroaryl, optionally substituted with a halogen, cyano, nitro, $C_{1-6}$-alk(en/yn)yl, $C_{1-6}$-alk(en/yn)yloxy, $C_{1-6}$-alk(en/yn)ylsulfanyl, hydroxy, hydroxy-$C_{1-6}$-alk(en/yn)yl, halo-$C_{1-6}$-alk(en/yn)yl, halo-$C_{1-6}$-alk(en/yn)yloxy, $C_{3-8}$-cycloalk(en)yl, $C_{3-8}$-cycloalk(en)yl-$C_{1-6}$-alk(en/yn)yl, acyl, $C_{1-6}$-alk(en/yn)yloxycarbonyl, $C_{1-6}$-alk(en/yn)ylsulfonyl or $-NR^{15}R^{16}$ wherein $R^{15}$ and $R^{16}$ are each independently hydrogen, $C_{1-6}$-alk(en/yn)yl, $C_{3-8}$-cycloalk(en)yl, $C_{3-8}$-cycloalk(en)yl-$C_{1-6}$ alk(en/yn)yl or aryl, or $R^{15}$ and $R^{16}$ together with the nitrogen atom to which they are attached form a 3-7-membered heterocyclic ring which optionally contains one further heteroatom selected from O, S and N;

$R^6$ is H, $C_{1-6}$-alk(en/yn)yl, $C_{1-6}$-alk(en/yn)yloxy, $C_{1-6}$-alk(en/yn)ylsulfanyl or $C_{3-8}$-cycloalk(en)yl, provided that when $R^6$ is $C_{1-6}$-alk(en/yn)yloxy or $C_{1-6}$-alk(en/yn)ylsulfanyl then X is $CR^{11}R^{12}$, wherein $R^{11}$ and $R^{12}$ are each independently H or $C_{1-6}$ alkyl;

$R^7$ and $R^8$ are each independently H, $C_{1-6}$-alk(en/yn)yl or $C_{3-8}$-cycloalk(en)yl;

$R^9$ and $R^{9'}$ are each independently H, $C_{1-6}$-alk(en/yn)yl, hydroxy-$C_{1-6}$-alk(en/yn)yl, $C_{1-6}$alk(en/yn)ylsulfanyl-$C_{1-6}$-alk(en/yn)yl or $C_{3-8}$-cycloalk(en)yl; or $R^6$ and $R^8$ together with the atoms to which they are attached and the intervening carbon atom form a saturated 3-7 membered heterocyclic ring, and $R^7$ is H, $C_{1-6}$-alk(en/yn)yl or $C_{3-8}$-cycloalk(en)yl, and $R^9$ and $R^{9'}$ are each independently H, $C_{1-6}$-alk(en/yn)yl, hydroxy-$C_{1-6}$-alk(en/yn)yl, $C_{1-6}$ alk(en/yn)ylsulfanyl-$C_{1-6}$-alk(en/yn)yl or $C_{3-8}$-cycloalk(en)yl; or $R^7$ and $R^8$ together with the atoms to which they are attached form a saturated 3-7 membered heterocyclic ring, and $R^6$ is H, $C_{1-6}$-alk(en/yn)yl, $C_{1-6}$-alk(en/yn)yloxy, $C_{1-6}$-alk(en/yn)ylsulfanyl or $C_{3-8}$-cycloalk(en)yl, provided that when $R^6$ is $C_{1-6}$-alk(en/yn)yloxy or $C_{1-6}$-alk(en/yn)ylsulfanyl then X is $CR^{11}R^{12}$, wherein $R^{11}$ and $R^{12}$ are each independently H or $C_{1-6}$ alkyl, and $R^9$ and $R^{9'}$ are each independently H, $C_{1-6}$-alk(en/yn)yl, hydroxy-$C_{1-6}$-alk(en/yn)yl, $C_{1-6}$ alk(en/yn)ylsulfanyl-$C_{1-6}$-alk(en/yn)yl or $C_{3-8}$-cycloalk(en)yl; or $R^8$ and $R^9$ together with the atoms to which they are attached and the intervening carbon atom form a saturated 3-7 membered heterocyclic ring, and $R^6$ is H, $C_{1-6}$-alk(en/yn)yl, $C_{1-6}$-alk(en/yn)yloxy, $C_{1-6}$-alk(en/yn)ylsulfanyl or $C_{3-8}$-cycloalk(en)yl, provided that when $R^6$ is $C_{1-6}$-alk(en/yn)yloxy or $C_{1-6}$-alk(en/yn)ylsulfanyl then X is $CR^{11}R^{12}$, wherein $R^{11}$ and $R^{12}$ are each independently H or $C_{1-6}$ alkyl, and $R^7$ is H, $C_{1-6}$-alk(en/yn)yl or $C_{3-8}$-cycloalk(en)yl, and $R^{9'}$ is H, $C_{1-6}$-alk(en/yn)yl, hydroxy-$C_{1-6}$-alk(en/yn)yl, $C_{1-6}$ alk(en/yn)ylsulfanyl-$C_{1-6}$-alk(en/yn)yl or $C_{3-8}$-cycloalk(en)yl;

$R^{10}$ is H, $C_{1-6}$-alk(en/yn)yl, aryl, aryl-$C_{1-6}$-alk(en/yn)yl, wherein aryl is optionally substituted with a halogen, $CF_3$, $OCF_3$, CN, $NO_2$ or $C_{1-6}$-alk(en/yn)yl, or an alkali metal;

or a pharmaceutically acceptable salt thereof.

2. The compound of claim 1 wherein X is O or $CH_2$.

3. The compound of claim 1 wherein Y is O.

4. The compound of claim 1 wherein Y is S.

5. The compound of claim 1 wherein $R^1$ is hydrogen, $C_{1-6}$-alkyl, halogen, phenyl, or phenyl substituted with one or two subtituents selected from $C_{1-6}$-alkyl and $C_{1-6}$-alkoxy.

6. The compound of claim 1 wherein $R^2$ is hydrogen; cyano; $C_{1-6}$-alkyl; halogen; phenyl; phenyl substituted with one or two subtituents selected from cyano, $C_{1-6}$-alkyl, $C_{1-6}$-alkoxy, and $C_{1-6}$-alkylsulfonyl; —$NR^{13}R^{14}$ wherein $R^{13}$ and $R^{14}$ together with the nitrogen atom to which they are attached form a 3-7-membered heterocyclic ring which optionally contains one further heteroatom selected from O, S and N; or monocyclic heteroaryl.

7. The compound of claim 1 wherein $R^3$ is hydrogen; $C_{1-6}$-alkyl; halogen; phenyl; phenyl substituted with one or two subtituents selected from cyano, $C_{1-6}$-alkyl, and $C_{1-6}$-alkoxy; or monocyclic heteroaryl.

8. The compound of claim 1 wherein $R^4$ is hydrogen, $C_{1-6}$-alkyl, halogen, phenyl or phenyl substituted with one or two substituents selected from $C_{1-6}$-alkyl and $C_{1-6}$-alkoxy.

9. The compound of claim 1 wherein $R^5$ is phenyl, optionally substituted with a halogen, $C_{1-6}$-alkyl, $C_{1-6}$-alkyloxy, $C_{1-6}$-alkylsulfanyl, or halo-$C_{1-6}$-alkyl.

10. The compound of claim 1 wherein $R^6$ from H or $C_{1-6}$-alkyl.

11. The compound of claim 1 wherein $R^7$ is H or $C_{1-6}$-alkyl.

12. The compound of claim 1 wherein $R^8$ is H, $C_{1-6}$-alkyl or $C_{3-8}$-cycloalkyl.

13. The compound of claim 1 wherein $R^9$ and $R^{9'}$ are each independently H or $C_{1-6}$-alkyl.

14. The compound of claim 1 wherein $R^{10}$ is H.

15. The compound of claim 1 wherein $R^6$ and $R^8$ together with the atoms to which they are attached and the intervening carbon atom form a 1-pyrrolidinyl, 1-piperidinyl or 1-azepinyl, optionally substituted with a $C_{1-6}$-alkyl, and $R^7$ is H, $C_{1-6}$-alk(en/yn)yl or $C_{3-8}$-cycloalk(en/yn)yl, and $R^9$ and $R^{9'}$ are each independently H, $C_{1-6}$-alk(en/yn)yl, hydroxy-$C_{1-6}$-alk(en/yn)yl, $C_{1-6}$ alk(en/yn)ylsulfanyl-$C_{1-6}$-alk(en/yn)yl or $C_{3-8}$-cycloalk(en)yl.

16. The compound of claim 1 wherein $R^7$ and $R^8$ together with the atoms to which they are attached form a 1-pyrrolidinyl, 1-piperidinyl or 1-azepinyl, optionally substituted with a $C_{1-6}$-alkyl, and $R^6$ is H, $C_{1-6}$-alk(en/yn)yl, $C_{1-6}$-alk(en/yn)yloxy, $C_{1-6}$-alk(en/yn)ylsulfanyl or $C_{3-8}$-cycloalk(en)yl, provided that when $R^6$ is $C_{1-6}$-alk(en/yn)yloxy or $C_{1-6}$-alk(en/yn)ylsulfanyl then X is $CR^{11}R^{12}$, wherein $R^{11}$ and $R^{12}$ are each independently from H or $C_{1-6}$ alkyl and $R^9$ and $R^{9'}$ are independently H, $C_{1-6}$-alk(en/yn)yl, hydroxy-$C_{1-6}$-alk(en/yn)yl, $C_{1-6}$ alk(en/yn)ylsulfanyl-$C_{1-6}$-alk(en/yn)yl or $C_{3-8}$-cycloalk(en)yl.

17. The compound of claim 1 wherein $R^8$ and $R^9$ together with the atoms to which they are attached and the intervening carbon atom form a 1-pyrrolidinyl, 1-piperidinyl or 1-azepinyl, optionally substituted with a $C_{1-6}$-alkyl, and $R^6$ is selected from H, $C_{1-6}$-alk(en/yn)yl, $C_{1-6}$-alk(en/yn)yloxy, $C_{1-6}$-alk(en/yn)ylsulfanyl or $C_{3-8}$-cycloalk(en)yl, provided that when $R^6$ is $C_{1-6}$-alk(en/yn)yloxy or $C_{1-6}$-alk(en/yn)ylsulfanyl then X is $CR^{11}R^{12}$, wherein $R^{11}$ and $R^{12}$ are each independently H or $C_{1-6}$ alkyl, and $R^7$ is selected from H, $C_{1-6}$-alk(en/yn)yl or $C_{3-8}$-cycloalk(en/yn)yl, and $R^{9'}$ is H, $C_{1-6}$-alk(en/yn)yl, hydroxy-$C_{1-6}$-alk(en/yn)yl, $C_{1-6}$ alk(en/yn)ylsulfanyl-$C_{1-6}$-alk(en/yn)yl or $C_{3-8}$-cycloalk(en)yl.

18. The compound of claim 1 selected from the group consisting of:

(S)-1-{2-[2-(4-Fluoro-phenylsulfanyl)-phenoxy]-ethyl}-pyrrolidine-2-carboxylic acid, (S)-1-{2-[2-(4-tert-Butyl-phenylsulfanyl)-phenoxy]-ethyl}-pyrrolidine-2-carboxylic acid, (S)-1-{2-[2-(4-Trifluoromethyl-phenylsulfanyl)-phenoxy]-ethyl}-pyrrolidine-2-carboxylic acid, (S)-1-{2-[2-(3-Fluoro-phenylsulfanyl)-phenoxy]-ethyl}-pyrrolidine-2-carboxylic acid, (S)-{2-[2-(4-Chloro-phenylsulfanyl)-phenoxy]-ethyl}-pyrrolidine-2-carboxylic acid, (S)-1-{2-[2-(3-Chloro-phenylsulfanyl)-phenoxy]-ethyl}-pyrrolidine-2-carboxylic acid, (S)-1-{2-[2-(3,4-Dichloro-phenylsulfanyl)-phenoxy]-ethyl}-pyrrolidine-2-carboxylic acid, (S)-1-{2-[2-(3-Chloro-4-fluoro-phenylsulfanyl)-phenoxy]-ethyl}-pyrrolidine-2-carboxylic acid, (S)-1-{2-[2-(3-Chloro-phenoxy)-phenoxy]-ethyl}-pyrrolidine-2-carboxylic acid, (S)-1-{2-[2-(4-Chloro-phenoxy)-phenoxy]-ethyl}-pyrrolidine-2-carboxylic acid, (S)-1-{2-[2-(4-Methoxy-phenoxy)-phenoxy]-ethyl}-pyrrolidine-2-carboxylic acid, (S)-1-{2-[2-(3,4-Difluoro-phenoxy)-phenoxy]-ethyl}-pyrrolidine-2-carboxylic acid, 1-{2(R/S)-[2-(4-Chloro-phenoxy)-phenoxy]-propyl}-pyrrolidine-2(S)-carboxylic acid, 1-{2(R/S)-[2-(3,4-Difluoro-phenoxy)-phenoxy]-propyl}-pyrrolidine-2(S)-carboxylic acid, (S)-1-{2-[2-(3-Fluoro-phenoxy)-phenoxy]-ethyl}-pyrrolidine-2-carboxylic acid, 1-{2(R/S)-[2-(3-Fluoro-phenoxy)-phenoxy]-propyl}-pyrrolidine-2(S)-carboxylic acid, 1-{2(R/S)-[2-(3-Fluoro-phenylsulfanyl)-phenoxy]-propyl}-pyrrolidine-2(S)-carboxylic acid, 1-{2(R/S)-[2-(3-Chloro-phenylsulfanyl)-phenoxy]-propyl}-pyrrolidine-2(S)-carboxylic acid, ({2-[2-(4-tert-Butyl-phenylsulfanyl)-phenoxy]-ethyl}-N-ethyl-amino)-acetic acid, 2-{3-[2-(4-tert-Butyl-phenylsulfanyl)-phenoxy]-pyrrolidin-1-yl}-propionic acid, ({2-[2-(3-Chloro-phenylsulfanyl)-phenoxy]-ethyl}-N-methyl-amino)-acetic acid, ({2-[2-(3-Chloro-4-fluoro-phenylsulfanyl)-phenoxy]-ethyl}-N-methyl-amino)-acetic acid, {2-[2-(4-tert-Butyl-phenylsulfanyl)-phenoxymethyl]-piperidin-1-yl}-acetic acid, ({2-[2-(3-Fluoro-phenylsulfanyl)-phenoxy]-ethyl}-N-methyl-amino)-acetic acid, {4-[2-(4-tert-Butyl-phenylsulfanyl)-phenoxy]-piperidin-1-yl}-acetic acid, (N-2-propyl-{2-[2-(4-trifluoromethyl-phenylsulfanyl)-phenoxy]-ethyl}-amino)-acetic acid, ({2-[2-(3,4-Dichloro-phenylsulfanyl)-phenoxy]-ethyl}-N-ethyl-amino)-acetic acid, (N-Ethyl-{2-[2-(4-methylsulfanyl-phenylsulfanyl)-phenoxy]-ethyl}-amino)-acetic acid, 2-{3-[2-(3,4-Dichloro-phenylsulfanyl)-phenoxy]-pyrrolidin-1-yl}-propionic acid, (S)-{3-[2-(4-tert-Butyl-phenylsulfanyl)-phenoxy]-pyrrolidin-1-yl}-acetic acid, ({2-[2-(3-Chloro-4-fluoro-phenylsulfanyl)-phenoxy]-ethyl}-N-ethyl-amino)-acetic acid, (N-2-propyl-{2-[2-(4-methylsulfanyl-phenylsulfanyl)-phenoxy]-ethyl}-amino)-acetic acid, {3-[2-(4-tert-Butyl-phenylsulfanyl)-phenoxy]-pyrrolidin-1-yl}-acetic acid, ({2-[2-(3-Chloro-phenylsulfanyl)-phenoxy]-ethyl}-N-ethyl-amino)-acetic acid, ({2-[2-(4-Chloro-phenylsulfanyl)-phenoxy]-ethyl-}N-methyl-amino)-acetic acid,
{4-[2-(3,4-Dichloro-phenylsulfanyl)-phenoxy]-piperidin-1-yl}-acetic acid,
2-{3-[2-(4-Trifluoromethyl-phenylsulfanyl)-phenoxy]-pyrrolidin-1-yl}-propionic acid,
({2-[2-(4-tert-Butyl-phenylsulfanyl)-phenoxy]-ethyl}-N-2-propyl-amino)-acetic acid
({2-[2-(4-tert-Butyl-phenylsulfanyl)-phenoxy]-ethyl}-N-methyl-amino)-acetic acid,
{2-[2-(4-Methylsulfanyl-phenylsulfanyl)-phenoxymethyl]-piperidin-1-yl}-acetic acid,
({2-[2-(3,4-Dichloro-phenylsulfanyl)-phenoxy]-ethyl}-N-methyl-amino)-acetic acid,
(N-Methyl-{2-[2-(4-trifluoromethyl-phenylsulfanyl)-phenoxy]-ethyl}-amino)-acetic acid,
2-{3(R)-[2-(4-tert-Butyl-phenylsulfanyl)-phenoxy]-pyrrolidin-1-yl}-propionic acid,
2-{3(R)-[2-(3,4-Dichloro-phenylsulfanyl)-phenoxy]-pyrrolidin-1-yl}-propionic acid,
2-[3(R)-(2-(4-methylphenyl)-sulfanyl-phenoxy)-pyrrolidin-1-yl]-propionic acid,
{3(R)-[2-(4-tert-Butyl-phenylsulfanyl)-phenoxy]-pyrrolidin-1-yl}-acetic acid,
2-{3(R)-[2-(4-Trifluoromethyl-phenylsulfanyl)-phenoxy]-pyrrolidin-1-yl}-propionic acid,
2-{3(R)-[2-(4-Chloro-phenylsulfanyl)-phenoxy]-pyrrolidin-1-yl}-propionic acid,
({1-[2-(3-Chloro-phenylsulfanyl)-phenoxymethyl]-propan-2yl}-N-ethyl-amino)-acetic acid,
({1-[2-(3,4-Dichloro-phenylsulfanyl)-phenoxy]-butan-2-yl}-N-ethyl-amino)-acetic acid,
({1-[2-(3,4-Dichloro-phenylsulfanyl)-phenoxy]-butan-3-methyl-2-yl}-N-ethyl-amino)-acetic acid,
({1-[2-(3-Chloro-4-fluoro-phenylsulfanyl)-phenoxy]-butan-2-yl}-N-ethyl-amino)-acetic acid,
({1-[1-(3-Chloro-phenylsulfanyl)-phenoxy]-propan-2-yl}-N-ethyl-amino)-acetic acid,
({1-[2-(3-Chloro-4-fluoro-phenylsulfanyl)-phenoxy]-butan-4-methyl-2-yl}-N-ethyl-amino)-acetic acid,
({1-[2-(3-Chloro-4-fluoro-phenylsulfanyl)-phenoxy]propan-2-yl}-N-ethyl-amino)-acetic acid,
(S)-({1-[2-(3-Chloro-phenylsulfanyl)-phenoxy]-propan-2-yl}-N-methyl-amino)-acetic acid,
(S)-({1-[2-(3-Chloro-phenylsulfanyl)-phenoxy]-propan-2-yl}-N-ethyl-amino)-acetic acid,
({1-[2-(3,4-Dichloro-phenylsulfanyl)-phenoxy]-propan-2-yl}-N-ethyl-amino)-acetic acid,
({1-[2-(4-Chloro-phenylsulfanyl)-phenoxy]-propan-2-yl}-N-ethyl-amino)-acetic acid,
({1-[2-(3-Chloro-phenylsulfanyl)-phenoxymethyl]-propyl}-N-methyl-amino)-acetic acid,
({1-[2-(4-Chloro-phenylsulfanyl)-phenoxymethyl]-propyl}-N-ethyl-amino)-acetic acid,
(N-Ethyl-{1-[2-(3-fluoro-phenylsulfanyl)-phenoxymethyl]-propyl}-amino)-acetic acid,
(R)-({2-[2-(3,4-Dichloro-phenylsulfanyl)-phenoxy]-1-methyl-ethyl}-N-ethyl-amino)-acetic acid,
(S)-2-{1-[2-(4-Chloro-phenoxy)-phenoxy]-propan-2-}-N-methyl-amino)-acetic acid,
(R)-(2-{1-[2-(3-Chloro-phenylsulfanyl)-phenoxy]-propan-2-yl}-N-methyl-amino)-acetic acid,
({2-[2-(3-Fluoro-phenylsulfanyl)-phenoxy]-propyl}-N-methyl-amino)-acetic acid,
({2-[2-(3-Chloro-phenylsulfanyl)-phenoxy]-propan-1yl}-N-ethyl-amino)-acetic acid,
({1-[2-(3-Chloro-phenylsulfanyl)-phenoxy]-3-methyl-butan-2-yl}-N-methyl-amino)-acetic acid,
({3-methyl-1-[2-(4-trifluoromethyl-phenylsulfanyl)-phenoxy]-butan-2-yl}-N-ethyl-amino)-acetic acid,
({1-[2-(3-Chloro-4-fluoro-phenylsulfanyl)-phenoxy]-butan-2-yl}-N-methyl-amino)-acetic acid,
(S)-({1-[2-(3-Chloro-4-fluoro-phenylsulfanyl)-phenoxy]-propan-2-yl}N-methyl-amino)-acetic acid,
(S)-({1-[2-(3-Fluoro-phenylsulfanyl)-phenoxy]-propan-2yl}-N-methyl-amino)-acetic acid,
({1-[2-(4-tert-Butyl-phenylsulfanyl)-phenoxy]-3-methyl-butan-2-yl}-N-ethyl-amino)-acetic acid,
(S)-({1-[2-(3,4-Dichloro-phenylsulfanyl)-phenoxy]-propan-2-yl}-N-methyl-amino)-acetic acid,
({1-[2-(3-Chloro-4-fluoro-phenylsulfanyl)-phenoxy]-3-methyl-butan-2-yl}-N-methyl-amino)-acetic acid,
({1-[2-(4-tert-Butyl-phenylsulfanyl)-phenoxy]-propan-2-yl}-N-ethyl-amino)-acetic acid,
({2-[2-(3-Chloro-4-fluoro-phenylsulfanyl)-phenoxy]-propan-1-yl}-N-ethyl-amino)-acetic acid,
({2-[2-(4-methoxy-phenylsulfanyl)-phenoxy]-propan-1-yl}-N-Cyclohexyl-amino)-acetic acid,
{[2-(2-(4-methyl-phenylsulfanyl-phenoxy)-propan-1-yl-]-N-cyclohexyl-amino}-acetic acid,
({2-[2-(3-Chloro-phenylsulfanyl)-phenoxy]-propan-1-yl}-N-cyclohexyl-amino)-acetic acid,
(S)-1-{3-[2-(3-Fluoro-phenylsulfanyl)-phenyl]-propyl}-pyrrolidine-2-carboxylic acid,
(S)-2-({2-[3-(3-Fluoro-phenylsulfanyl)-biphenyl-4-yloxy]-ethyl}-methyl-amino)-propionic acid,
({2-[3-(3-Fluoro-phenylsulfanyl)-biphenyl-4-yloxy]-ethyl}-methyl-amino)-acetic acid,
(S)-1-{2-[4-Chloro-2-(3-fluoro-phenylsulfanyl)-phenoxy]-ethyl}-pyrrolidine-2-carboxylic acid,
(S)-1-{2-[3-Chloro-2-(3-fluoro-phenylsulanyl)-phenoxy]-ethyl}pyrrolidine-2-carboxylic acid,
(S)-1-{2-[5-Chloro-2-(3-fluoro-phenylsulfanyl)-phenoxy]-ethyl}pyrrolidine-2-carboxylic acid,
(S)-1-{2-[4-Cyano-2-(3-fluoro-phenylsulfanyl)-phenoxy]-ethyl}-pyrrolidine-2-carboxylic acid
(S)-1-[2-(5-Chloro-2-phenylsulfanyl-phenoxy)-ethyl]pyrrolidine-2-carboxylic acid,
(S)-1-{2-[3-(3-Fluoro-phenylsulfanyl)-biphenyl-4-yloxy]-ethyl}-pyrrolidine-2-carboxylic acid,
(S)-{2-[4'-Methoxy-3-(3-fluoro-phenylsulfanyl)-biphenyl-4-yloxy]-ethyl}-pyrrolidine-2-carboxylic acid,
(S)-{2-[4'-Cyano-3-(3-fluoro-phenylsulfanyl)-biphenyl-4-yloxy]-ethyl}-pyrrolidine-2-carboxylic acid,
(S)-1-{2-[4'-Cyano-4-(3-fluoro-phenylsulfanyl)-biphenyl-3-yloxy]-ethyl}-pyrrolidine-2-carboxylic acid,
(S)-1-{2-[2-(3-Fluoro-phenylsulfanyl)-5-thiophen-3-yl-phenoxy]-ethyl}-pyrrolidine-2-carboxylic acid,
(S)-1-{2-[2-(3-Fluoro-phenylsulfanyl)-4-pyrimidin-5-yl-phenoxy]-ethyl}-pyrrolidine-2-carboxylic acid,
(S)-1-{2-[3-(3-Fluoro-phenylsulfanyl)-3-methanesulfonyl-biphenyl-4-yloxy]-ethyl}-pyrrolidine-2(S)-carboxylic acid,
(S)-1-{2-[2-(3-Fluoro-phenylsulfanyl)-4-morpholin-4-yl-phenoxy]-ethyl}-pyrrolidine-2-carboxylic acid, and
(S)-1-{2-[2-(3-Fluoro-phenylsulfanyl)-4-piperidin-1-yl-phenoxy]-ethyl}-pyrrolidine-2-carboxylic acid, or a pharmaceutically acceptable salt thereof.

19. A pharmaceutical composition comprising a compound according to claim 1 and a pharmaceutically acceptable carrier or diluent.

20. A method for the treatment of schizophrenia comprising administering to a subject in need thereof a therapeutically effective amount of a compound according to claim 1.

21. The method of claim 20, wherein said method is for the treatment of the positive symptoms, negative symptoms, or both the positive and negative symptoms of schizophrenia.

22. The method of claim 20 wherein said subject is a human.

23. A pharmaceutical composition comprising a compound according to claim 18 and a pharmaceutically acceptable carrier or diluent.

* * * * *